(12) United States Patent
Bashkin et al.

(10) Patent No.: US 9,133,228 B2
(45) Date of Patent: Sep. 15, 2015

(54) GUANIDINYL-SUBSTITUTED POLYAMIDES USEFUL FOR TREATING HUMAN PAPILLOMA VIRUS

(71) Applicants: Nanovir, LLC, Kalamazoo, MI (US); The Curators of the University of Missouri, Columbia, MO (US)

(72) Inventors: James Bashkin, St. Louis, MO (US); Terri G. Edwards, Kalamazoo, MI (US); Christopher Fisher, Kalamazoo, MI (US); George D. Harris, Jr., Chesterfield, MO (US); Kevin J. Koeller, Richmond Heights, MO (US)

(73) Assignees: NanoVir LLC, Kalamazoo, MI (US); THE CURATORS OF THE UNIVERSITY OF MISSOURI, Columbia, MO (US)

( * ) Notice: Subject to any disclaimer, the term of this patent is extended or adjusted under 35 U.S.C. 154(b) by 207 days.

(21) Appl. No.: 13/649,000

(22) Filed: Oct. 10, 2012

(65) Prior Publication Data

US 2013/0090362 A1   Apr. 11, 2013

Related U.S. Application Data

(60) Provisional application No. 61/545,311, filed on Oct. 10, 2011.

(51) Int. Cl.
*A61K 31/47* (2006.01)
*C07H 1/00* (2006.01)
*C07K 14/00* (2006.01)

(52) U.S. Cl.
CPC .............. *C07H 1/00* (2013.01); *C07K 14/003* (2013.01)

(58) Field of Classification Search
USPC ..................... 514/386, 422; 548/314.7, 518
See application file for complete search history.

(56) References Cited

U.S. PATENT DOCUMENTS

| | | | |
|---|---|---|---|
| 5,616,606 A | 4/1997 | Lown et al. | |
| 6,673,940 B1 | 1/2004 | Dervan et al. | |
| 6,958,240 B1 | 10/2005 | Baird et al. | |
| 7,589,171 B2 | 9/2009 | Bashkin et al. | |
| 8,119,677 B2 | 2/2012 | Bashkin et al. | |
| 8,524,899 B2 | 9/2013 | Dervan et al. | |
| 2003/0109448 A1 | 6/2003 | Crowley et al. | |
| 2003/0119891 A1 | 6/2003 | Phillion et al. | |
| 2004/0171799 A1 | 9/2004 | Sugiyama et al. | |
| 2005/0009054 A1 | 1/2005 | Phillion et al. | |
| 2008/0287318 A1 | 11/2008 | Kranewitter et al. | |
| 2012/0225809 A1 | 9/2012 | Bashkin et al. | |

FOREIGN PATENT DOCUMENTS

| | | |
|---|---|---|
| WO | WO9835702 | 8/1998 |
| WO | WO9837066 | 8/1998 |
| WO | WO9837067 | 8/1998 |
| WO | WO9850058 | 11/1998 |
| WO | WO0015773 | 3/2000 |
| WO | WO2004099131 | 11/2004 |
| WO | 2005-033282 | 4/2005 |
| WO | WO2005033282 | 4/2005 |
| WO | WO2007045096 | * 4/2007 |
| WO | WO2007103584 | 9/2007 |
| WO | 2007-130616 | 11/2007 |
| WO | WO2007130616 | * 11/2007 |

OTHER PUBLICATIONS

Edwards TG, Koeller KJ, Slomczynska U, Fok K, Helmus M, Bashkin JK, et al. HPV Episome Levels are Potently Decreased by Pyrrole-Imidazole Polyamides. Antiviral Res. 2011;91(2):177-86.
Yasuda A, Noguchi K, Minoshima M, Kashiwazaki G, Kanda T, Katayama K, et al. DNA ligand designed to antagonize EBNA1 represses epstein-barr virus-induced immortalization. Cancer Sci. 2011;102(12):2221-30.
Khalaf AI, Anthony N, Breen D, Donoghue G, Mackay SP, Scott FJ, et al. Amide isosteres in structure-activity studies of antibacterial minor groove binders. European Journal of Medicinal Chemistry. 2011;46(11):5343-55.
Jacobs CS, Dervan PB. Modifications at the C-Terminus to Improve Pyrrole—Imidazole Polyamide Activity in Cell Culture. J Med Chem. 2009;52(23):7380-7388.
Muzikar KA, Meier JL, Gubler DA, Raskatov JA, Dervan PB. Expanding the Repertoire of Natural Product-Inspired Ring Pairs for Molecular Recognition of DNA. Org Lett. 2011;13(20):5612-5.
PCT International Search Report dated Jun. 13, 2013, International Application No. PCT/US2012/059604.
Martinez, Thomas, F., et al., Replication stress by Py-Im polyamides induces a non-canonical ATR-dependent checkpoint response, Nucleic Acids Research, Sep. 23, 2014, pp. 1-14.
Philips, Brian, J., et al., DNA Damage effects of a polyamide-CBI conjugate in SV40 virions, Molecular Pharmacology, 67, 2005, pp. 877-882.
Wang, Tong-Dong, et al., DNA crosslinking and biological activity of a hairpin polyamide-chlorambucil conjugate, Nucleic Acids Research, vol. 31, No. 4, 2003, pp. 1208-1215.
Buchmueller, et al., "Molecular recognition of DNA base pairs by the formamido pyrrole and formamido imidazole pairings in stacked polyamides", Nucleic Acids Research, 912-921, 2005, vol. 33, No. 3.
Coull, et al., "Targeted Derepressioin of the Human Immunodeficiency Virus Type 1 Long Terminal Repeat by Pyrrole-Imidazole Polyamides", Journal of Virology, Dec. 2002, pp. 12349-12354.
Crowley, et al., "Controlling the Intracellular Localization of Fluorescent Polyamide Analogues in Cultured Cells", Bioorganic & Medicinal Chemistry Letters, 13, 2003, pp. 1565-1570.
Dervan, et al., "Recognition of the DNA minor groove by pyrrole-imidazole polyamides" Current Opinion in Structural Biology, 2003, 13, pp. 284-299.

(Continued)

*Primary Examiner* — Rei-Tsang Shiao
(74) *Attorney, Agent, or Firm* — Hueschen and Sage

(57) ABSTRACT

Polyamide compositions containing guanidinyl radicals, including tetramethylguanidinyl radicals, are described. These polyamides are useful for medical applications, for example, for treating human papilloma virus infections.

13 Claims, 10 Drawing Sheets

(56) References Cited

OTHER PUBLICATIONS

Edelson, et al., "Influence of structure variation on nuclear localization of DNA-binding polyamide-fluorophore conjugates", Nucleic Acids Research, 2004, vol. 32, No. 9, pp. 2802-2818.

Groeger, K et al., Guanidiniocarbonyl-pyrrole-aryl conjugates as nucleic acid sensors: switch of binding mode and spectroscopic responses by introducing additional binding sites into the linker. Org. Biomol. Chem., vol. 9, pp. 198-209, 2011.

Livengood, et al., Paradoxical effects of DNS binding polyarnides on HTLV-1 transcription, Frontiers in Bioscience, 9, Sep. 1, 2004, pp. 3056-3067.

Lown, et al., "Novel linked antiviral and antitumor agents related to netropsin and distamycin. Synthesis and biological evaluation", J. Med. Chem., 1989, 32. pp. 2368-2375.

Marques, et al., "Expanding the Repertoire of Heterocycle Ring Pairs for Programmable for Minor Groove DNA Recognition", J. Am. Chem. Soc., 2004, 126, pp. 10339-10349.

Nickols, et al, "Improved nuclear localization of DNA-binding polyamides", Nucleic Acids Research, 2007, vol. 35, No. 2, pp. 363-370.

Nishijima, S., et al., "Cell permeability of Py-Im-polyamide-fluorescein conjugates: Influence of molecular size and Py/Irn content", Bioorganic & Medicinal Chemistry, 2010, 18, pp. 978-983.

O'Hare, et al., "DNA sequence recognition in the minor groove by crosslinked polyamides The effect of N-terminal head group and linker length on binding affinity and specificty", Proc. Natl. Acad. Sci. USA, 2002, vol. 99, No. 1, pp. 72-77.

Renneberg, et al., "Imidazopyridine Pyrrole and Hydroxybenzimidazole Pyrrole Pairs for DNA Minor Groove Recognition", J. Am. Chem. Soc., 2003, 125, pp. 5707-5716.

Schaal, et al., "Inhibition of human papilloma virus E2 DNA binding protein by covalently linked polyamides", Nucleic Acids Research, vol. 31, No. 4, 2003, pp. 1282-1291.

Tsai, et al., "Unanticipated differences between {alpha}—and {gamma}—diaminobutyric acid-linked hairpin polyamide-alkylator conjugates", Nucleic Acids Research. 2007, vol. 35, No. 1, pp. 307-316.

Turner, et al., "Aliphatic Aromatic Amino Acid Pairings for Polyamide Recognition in the Minor Groove of DNA", J. Am. Chem. Soc., 1998, 120, pp. 6219-6226.

Turner, et al., "Recognition of Seven Base Pair Sequences in the Minor Groove of DNA by Ten-Ring Pyrrole-Imidazole Polyamide Hairpins", J. Am. Chem. Soc., 1997, 119, pp. 7636-7644.

White, Peter, et al., "Inhibition of Human Papillomavirus DNA Replication by Small Molecule Antagonists of the E1 E2 Protein Interaction", The Journal of Biological Chemistry, vol. 278, No. 29, Jul. 18, 2003, pp. 26765-26772.

Zhan, et al., "Alternative heterocycles for dna recognition. a 3-pyrazole pyrrols pair specifies for g-c base pairs", Bioorganic & Medicinal Chemistry. 2000, 8, pp. 2467-2474.

Zhang, et al., "Discrimination of Hairpin Polyamides with an α-Substituted-γ-aminobutyric Acid as a 5'-TG-3' Reader in DNA Minor Groove", J. Am. Chem. Soc., 2006, 128, pp. 8766-8776.

Extended European Search Report for EP12840685.7 dated Mar. 10, 2015.

\* cited by examiner

Guanidinyl Radical $R^{1-4} = H$

Tautomer $R^1$ = alkyl, aryl, aralkyl
$R^{2-4} = H$

Tautomers $R^{1,2}$ = alkyl, aryl, aralkyl
$R^{3,4} = H$

Tautomer $R^{1,3}$ = alkyl, aryl, aralkyl
$R^{2,4}$ = H

Tautomers (equivalent when $R^1 = R^3$)

$R^{1-3,5}$ = alkyl, aryl, aralkyl
$R^4$ = H

Tautomer

Alkylated analog
of tautomer to the left $R^{1-4}$ = alkyl, aryl, aralkyl

Red Box: Reference peak  Black boxes: Foot printing peaks

GUANIDINYL-SUBSTITUTED POLYAMIDES USEFUL FOR TREATING HUMAN PAPILLOMA VIRUS

CROSS-REFERENCES TO RELATED APPLICATIONS

This application claims the benefit of the following provisional application, the entire disclosure of which is incorporated herein by reference for all purposes: U.S. Prov. App. No. 61/545,311 filed Oct. 10, 2011 by James K. Bashkin et al. and entitled "GUANIDINYL-SUBSTITUTED POLYAMIDES USEFUL FOR TREATING HUMAN PAPILLOMA VIRUS."

STATEMENT REGARDING FEDERALLY SPONSORED RESEARCH OR DEVELOPMENT

This invention was made with support under NIH grant 2R42AI068159, awarded by the National Institute of Allergy and Infectious Diseases (NIAID), part of the National Institutes of Health; the United States federal government, therefore, has certain rights in the invention.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

The present invention relates to polyamide compounds and the therapeutic uses of such compounds, such as therapies for treatment of subjects infected with human papilloma virus (HPV).

2. Description of Related Art

Human papilloma virus is a small double-stranded DNA virus that colonizes various stratified epithelia like skin, oral and genital mucosa, and induces the formation of self-limiting benign tumors known as papillomas (warts) or condylomas. Most of these benign tumors naturally regress due to the influence of host immunological defenses. Some HPVs, however, have oncogenic potential and have been associated with certain types of cancers. See, Lorincz et al., *Obstetrics & Gynecology,* 79:328-337 (1992); Beaudenon et al., *Nature,* 321:246-249 (1986); and Holloway et al., *Gynecol. One.,* 41:123-128 (1991).

HPV is the most prevalent, sexually transmitted virus. More than 35 HPV genotypes are known to be sexually transmitted, but a subset accounts for the majority of ano-genital infections. Among these most common HPV types are two forms with high risk for carcinogenic progression (HPV16 and HPV18), and two forms that cause the majority of genital warts (HPV6 and HPV11).

An estimated 5.5 million people become infected with HPV each year in the United States, and an estimated 20 million Americans are currently infected (Cates and et al., *Lancet,* 354, Suppl. SIV62, 1999). Approximately 75 percent of the male and female reproductive-age population has been infected with sexually transmitted HPV, though the main public health risk is to women through cervical cancer (Koutsky, *Am. J. Med.,* 102(5A), 3-8, 1997). Thus, millions of people in the U.S. alone require treatment each year. It is important to note that PAP smears represent the largest public health screening program in the world, and that the test is, essentially, a measure of HPV infection. The current standard for managing a positive PAP smear is "follow up". In general, no treatment is recommended unless an advanced stage of cervical dysplasia is observed (CDC Sexually Transmitted Diseases Treatment Guidelines, 2002).

Significant need exists in HPV positive subjects for effective HPV antiviral drugs. At present, no specific treatments exist for HPV or warts. Aldara™ (Imiquimod), an immunomodulator used for treating external genital warts, is the most successful treatment on the market. An effective, specific HPV treatment has the potential to significantly improve upon, and effectively compete with, Imiquimod.

The majority of human cervical carcinomas (95%) contain and express HPV DNA and it is the expression of two viral oncoproteins, E6 and E7 that appears to be critical for cellular transformation and maintenance of the transformed state. Specifically, four HPV types (HPV-16, HPV-18, HPV-31, and HPV-45) have been connected to 75-93% of the cases of cervical cancer in the United States. It has been estimated that perhaps twenty percent (20%) of all cancer deaths in women worldwide are from cancers that are associated with HPV.

HPV also causes anal cancer, with about 85 percent of all cases caused by HPV-16. HPV types 16 and 18 have also been found to cause close to half of vaginal, vulvar, and penile cancers.

Most recently, HPV infections have been found to cause cancer of the oropharynx, which is the middle part of the throat including the soft palate, the base of the tongue, and the tonsils. In the United States, more than half of the cancers diagnosed in the oropharynx are linked to HPV-16.

HPVs are grouped into types based on the uniqueness of their DNA sequence.

HPVs can be further classified as either high or low risk based on the clinical lesions with which they are associated or the relative propensity for these lesions to progress to cancer. Low risk cutaneous types, such as HPV types HPV-1, HPV-2, HPV-3, HPV-4, HPV-5, HPV-7, HPV-8, and HPV-9 cause common warts (verrucae vulgaris), plantar warts (verrucae plantaris), mosaic warts, flat warts (verrucae plane), and butcher warts. Furthermore, HPV types HPV-6 and HPV-11 cause warts of the external genitalia, anus and cervix. High-risk types, such as HPV-16, HPV-18, HPV-31, HPV-33 and HPV45 are particularly common in intraepithelial carcinomas, neoplasias and cancers. In particular, the genomes of two HPV types, HPV-16 and HPV-18, have been found to be associated with about 70 invasive carcinomas of the uterine cervix, as well as cancers of the oro-pharynx, anus, and other mucosal tissues.

Current treatment for HPV infection is extremely limited. Management normally involves physical destruction of the wart by surgical, cryosurgical, chemical, or laser removal of infected tissue. Some of these current treatments, like laser removal and surgery, are expensive and require the use of anesthesia to numb the area to be treated. Cryosurgical removal requires the use of special equipment. Furthermore, most subjects experience moderate pain during and after the procedure.

Topical creams and solutions such as preparations of 5-fluorouracil, Imiquimod, cidofovir, formaldehyde, glutaral, cimetidine, tricholoroacetic acid, bleomycin, podofilox and podophyllum preparations have also been used. (Reichman in Harrison's 7 Principles of Internal Medicine, 13th Ed. (Isselbacher et al., eds.); McGraw-Hill, Inc., NY (1993) pp.

801-803). Recurrence after these treatments, however, is common, most likely because the virus remains latent within the host epithelial cells. Therefore, subsequent repetitive treatments must be used, which can destroy healthy tissue. These treatments are not available or approved for treatment of cervical infections.

Interferon has also been employed as a treatment for persistent HPV infections and warts. However, its effectiveness is limited. Chang et al. (2002) *Journal of Virology* 76: 8864-74, found some cells infected with HPV genomes became resistant to interferon treatment after only a few applications. See also Cowsert (1994) *Intervirol.* 37:226-230; Bornstein et al. (1993) *Obstetrics Gynecol. Sur.* 4504:252-260; Browder et al. (1992) *Ann. Pharmacother.* 26:42-45.

Thus, there is a need for therapeutics for treating a number of diseases and conditions as outlined herein.

BRIEF SUMMARY OF THE INVENTION

The present invention provides polyamides, polyamide-containing compositions, methods for treating HPV infected cells, and methods for treating subjects infected with HPV. In some embodiments, the polyamide antiviral agents are well suited for treating laryngeal papillomatosis, cervical dysplasia and cancer and recurrent respiratory papillomatosis (RRP).

The polyamides of the present invention may be generally described as polymeric or oligomeric molecules containing a plurality of carboxamide repeating units such as those represented in FIG. 1 and at least one guanidinyl radical per molecule. In one embodiment, the polyamide is a compound having a polyamide backbone containing an interior unit selected from γ-aminobutyric acid (γ); 2,4-diaminobutyric acid ($\gamma_{NH2}$), which may be either the (R) or (S) isomer and which may be linked in to the backbone of the polyamide through either the 2-amino group (to form an alpha turn) or through the 4-amino group (to form a gamma turn); or $H_2N(CH_2)_2CH(NHC(=O)NHR)CO_2H$ (either the (R) or (S) isomer), wherein R is —$(CH_2)_3$—$N(CH_3)$—$(CH_2)_3$—$NH_2$ ($\gamma_{NHR'}$) or —$(CH_2)_3$—$N(CH_3)_2$ ($\gamma_{NHR''}$), and at least one guanidinyl radical pendant to 2,4-diaminobutyric acid ($\gamma_{NH2}$), and/or pendant to $H_2N(CH_2)_2CH(NHC(=O)NHR)CO_2H$, wherein R is —$(CH_2)_3$—$N(CH_3)$—$(CH_2)_3$—$NH_2$ ($\gamma_{NHR'}$), and/or at a terminal position of the polyamide backbone. The compound may be a pharmaceutically acceptable salt of such a polyamide. In the context of this invention, "interior" means at a position along the polymer backbone other than the terminal (end) positions or immediately adjacent to the terminal positions. The polyamide backbone may, in addition to the aforementioned interior unit, contain a plurality of units (for example, 5 to 30, or 7 to 28, or 9 to 24, or 11 to 22 or 15 to 21 or 16 to 21 units) selected from the group consisting of 4-amino-2-carbonyl-N-methylimidazole (Im), 4-amino-2-carbonyl-N-methylpyrrole (Py) and β-alanine (B).

In one aspect of the invention, the guanidinyl radical is connected to a terminal 4-amino-2-carbonyl-N-methylpyrrole (Py) unit (i.e., the primary amine group initially present in the Py unit becomes part of the guanidinyl radical). In another aspect of the invention, a des-aminoimidazole (des-Im, Formula XI, FIG. 1) forms the amino-terminus of the molecule and a guanidinyl radical is attached to an amino group elsewhere in the molecule, on for example the Ta or $\gamma_{NH2}$ group.

In other aspects of the invention, the guanidinyl radical may be unsubstituted or substituted. That is, the three nitrogen atoms present in the guanidinyl radical may bear substituents other than hydrogen. Such substituents may be, for example, alkyl, aralkyl and/or aryl groups. Examples of these variously substituted guanidinyl radicals and their related tautomers are shown in FIGS. 8A and 8B. In one embodiment of the invention, two of the nitrogen atoms each bear two alkyl groups, such as C1-C4 alkyl groups. For example, the guanidinyl radical may be tetramethylguanidinyl (TMG).

The compound may contain a C terminus end group selected from 3,3'-diamino-N-methyldipropylamine (Ta) or 3-(dimethylamino)propylamine (Dp).

In some embodiments, the invention provides a compound of the formula:

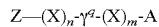

or a pharmaceutically acceptable salt thereof, wherein
  m is 3-16 (or 4-15, or 5-14, or 6-13 or 7-12);
  n is 2-14 (or 3-13, or 3-12, or 4-12, or 4-10);
  Z is guanidinylated 4-amino-2-carbonyl-N-methylpyrrole, N-formylated 4-amino-2-carbonyl-N-methylpyrrole, N-acetylated 4-amino-2-carbonyl-N-methylpyrrole, or des-aminoimidazole (des-Im, Formula XI, FIG. 1);
  each X is independently selected from 4-amino-2-carbonyl-N-methylimidazole (Im, Formula II, FIG. 1), 4-amino-2-carbonyl-N-methylpyrrole (Py, Formula I, FIG. 1) or β-alanine (β, Formula III, FIG. 1);
  $\gamma^q$ is γ-aminobutyric acid (γ, Formula IV, FIG. 1); 2,4-diaminobutyric acid ($\gamma_{NH2}$, corresponding to Formula V in FIG. 1 when the 2,4-diaminobutyric acid is the (R) isomer and linkage into the polyamide takes place through the γ amino group); guanidinylated 2,4-diaminobutyric acid; or
  $H_2N(CH_2)_2CH(NHC(=O)NHR)CO_2H$, wherein R is —$(CH_2)_3$—$N(CH_3)$—$(CH_2)_3$—$NH_2$ ($\gamma_{NHR'}$, Formula VIII, FIG. 1), guanidinylated —$(CH_2)_3$—$N(CH_3)$—$(CH_2)_3$—$NH_2$, or —$(CH_2)_3$—$N(CH_3)_2$ ($\gamma_{NHR''}$, Formula IX, FIG. 1);
  A is 3,3'-diamino-N-methyldipropylamine (Ta, Formula VII, FIG. 1), guanidinylated 3,3'-diamino-N-methyldipropylamine; or 3-(dimethylamino)propylamine (Dp, Formula VI, FIG. 1);

wherein the compound contains at least one primary amine group that has been guanidinylated.

In other embodiments, the invention provides a compound of the formula:

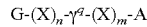

or a pharmaceutically acceptable salt thereof, wherein
  m is 5-12;
  n is 4-10;
  G is a guanidinyl radical;
  each X is independently selected from 4-amino-2-carbonyl-N-methylimidazole (Im, Formula II, FIG. 1), 4-amino-2-carbonyl-N-methylpyrrole (Py, Formula I, FIG. 1) or β-alanine (β, Formula III, FIG. 1);
  $\gamma^q$ is γ-aminobutyric acid (γ, Formula IV); 2,4-diaminobutyric acid ($\gamma_{NH2}$, corresponding to Formula V when the 2,4-diaminobutyric acid is the (R) isomer and linkage into the polyamide takes place through the γ amino group);
  or $H_2N(CH_2)_2CH(NHC(=O)NHR)CO_2H$, wherein R is —$(CH_2)_3$—$N(CH_3)$—$(CH_2)_3$—$NH_2$ ($\gamma_{NHR'}$, Formula VIII) or —$(CH_2)_3$—$N(CH_3)_2$ ($\gamma_{NHR''}$, Formula IX); and
  A is 3,3'-diamino-N-methyldipropylamine (Ta, Formula VII) or 3-(dimethylamino)propylamine (Dp, Formula VI).

In certain embodiments, m is 10 or 11. In other embodiments, m is 5, 6, 7, 8, or 9. In other embodiments, n is 7, 8, or 9. In other embodiments, n is 4, 5 or 6. In still other embodiments, the compound contains no more than 2, or no more than 1, Im units per molecule. In another embodiment, the compound does not contain any Im units in the structural sequence —(X)$_m$— and/or in the structural sequence —(X)$_n$—. The structural sequence —(X)$_n$— may, in certain embodiments, contain 1, 2 or 3β units. If the structural sequence —(X)$_n$— or —(X)$_m$— contains more than one β unit, all such units may be separated by at least one Im and/or Py unit. The polyamide may contain a β unit adjacent to the end group A. The polyamide may contain a Py unit adjacent to the other end group G. The structural sequence —(X)$_m$— may, in certain embodiments, contain 2, 3, 4 or 5β units. The polyamide compound may, in certain embodiments of the invention, be characterized by the absence of β units adjacent to each other.

In other embodiments, the compound can be:
TMG-PyβPyPyβPyIm-γ$_{NH2}$-PyβPyPyβPyPyPyβPyPy-Ta;
TMG-PyPyPyβPyPyβPyIm-γ$_{NHR'}$-PyβPyPyβPyPyPyβPyβ-Ta;
TMG-PyPyPyβPyPyβPyIm-γ$_{NH2}$-PyβPyPyβPyPyPyβPyβ-Ta;
TMG-PyPyPyβPyPyβPy-γ$_{NHR}$'-PyPyPyβPyPyPyβPyβ-Ta;
TMG-PyPyPyβPyPyβPyIm-γ$_{NH2}$-PyβPyPyβPyPyPyβPyβ-Dp;
TMG-PyPyPyβPyPyβPy-γ$_{NH2}$-PyPyPyβPyPyPyβPyβ-Ta;
TMG-PyPyPyβPyPyβPy-γ$_{NH2}$-PyPyPyβPyPyPyβPyβ-Dp;
TMG-PyβPyPyImβPyPy-γ-PyPyβPyPyPyβPyPyPyβ-Ta;
TMG-PyPyPyβPyPyβPy-γ$_{NHR''}$-PyPyPyβPyPyPyβPyβ-Dp;
TMG-PyβPyPyImβPyPy-γ-PyPyβPyPyPyβPyPyPyβ-Dp;
TMG-PyPyβPyPyPy-γ-PyPyβPyPyPyPyβ-Dp;
TMG-PyPyβPyPyPy-γ-PyPyβPyPyPyPyβ-Ta;
TMG-PyPyβPyPyImβPyPy-γ-PyPyβPyPyPyβPyPyPyβ-Ta;
TMG-PyPyβPyPyImβPyPy-γ-PyPyβPyPyPyβPyPyPyβ-Dp;
TMG-PyPyPyβPyPyβPyIm-γ-PyPyPyβPyPyPyβPyβ-Ta;
TMG-PyPyPyβPyPyβPyIm-γ-PyPyPyβPyPyPyβPyβ-Dp;
TMG-PyPyβPyPyβPyIm-γ-PyβPyPyβPyPyPyβPyβ-Dp;
TMG-PyPyβPyPyβPyIm-γ-PyβPyPyβPyPyPyβPyβ-Ta;
TMG-PyPyβPyPyβPy-γ$_{NH2}$-PyPyPyβPyPyPyβPyβ-Ta;
TMG-PyPyβPyPyβPyIm-γ$_{NH2}$-PyβPyPyβPyPyPyβPyβ-Ta;
TMG-PyPyβPyPyβPy-γ-PyPyPyβPyPyPyβPyβ-Ta;
TMG-PyPyPyβPyPyβPy-γ-PyPyPyβPyPyPyβPyβ-Ta;
or a pharmaceutically acceptable salt thereof or a mixture thereof.

In another embodiment, the invention provides a pharmaceutical composition comprising a therapeutically effective amount of one or more compounds described above and a pharmaceutically acceptable carrier.

In an aspect of the embodiment, the composition further comprises an anti-viral agent. The anti-viral agent can be, for example, an Interferon, Imiquimod, cidofovir, formaldehyde, glutaral, cimetidine, 5-fluorouracil, trichloroacetic acid, bleomycin, podofilox or podophyllum.

In another embodiment, the invention provides a method for binding double-stranded DNA in a sequence-specific manner, comprising contacting a DNA-target sequence within said DNA with a DNA-binding compound of one or more compounds described herein, in conditions allowing said binding to occur. The method may be carried out in vivo, in vitro or ex vivo. Further, it may be carried out in a cell, and the double stranded DNA may endogenous or heterologous to the cell.

Polyamide binding affinity and sequence specificity may be determined via qualitative and quantitative footprint titration experiments known in the art (see Brenowitz, M.; Senear, D. F.; Shea, M. A.; Ackers, G. K. *Methods Enzymol.* 1986, 130, 132; Mitra, S.; Shcherbakova, I. V.; Altman, R. B.; Brenowitz, M.; Laederach, A. *Nucl. Acids Res.* 2008, 36, e63; White, S.; Baird, E. E.; Dervan, P. B. *Biochemistry* 1996, 35, 12532; and White, S.; Baird, E. E.; Dervan, P. B. Chemistry & Biology 1997, 4, 569; all of which are incorporated herein by reference.)

Polyamides of the present invention may useful for detecting the presence of double stranded DNA of a specific sequence for diagnostic or preparative purposes. The sample containing the double stranded DNA may be contacted by polyamide linked to a solid substrate, thereby isolating DNA comprising a desired sequence. Alternatively, polyamides linked to a suitable detectable marker, such as biotin, a hapten, a radioisotope or a dye molecule, can be contacted by a sample containing double stranded DNA.

In yet another embodiment, the invention provides a method of reducing or inhibiting proliferation of neoplastic cells, comprising contacting the cells with an effective amount of one or more compounds described above. These neoplastic cells may be cancer cells, including selected from the group consisting of colon carcinoma cells, hepatocellular carcinoma cells, cervical carcinoma cells, lung epidermocarcinoma cells, mammary gland adenocarcinoma cells, pancreatic carcinoma cells, prostatic carcinoma cells, osteosarcoma cells, melanoma cells, acute promyelocytic leukemia cells, acute lymphoblastic leukemia cells, hepatocancreatico adenocarcinoma cells and Burkitt's lymphoma B cells.

The present invention further provides a method of treating virus infected cells comprising contacting the cells with an effective amount of a polyamide in accordance with the invention. The virus may be HPV, or other double-stranded DNA viruses. A subject infected with HPV may be treated by a method, which comprises administering to the subject an effective amount of a polyamide having a structure as described herein. The polyamide compound may be administered in the form of a pharmaceutical composition comprising the compound and a pharmaceutically acceptable carrier.

In still another embodiment, the invention provides a method of treating HPV infected cells comprising contacting the cells with a compound described herein. In an aspect of the invention, the method further comprises contacting the cells with an anti-viral agent. The anti-viral agent can be, for example, an Interferon, Imiquimod, cidofovir, formaldehyde, glutaral, cimetidine, 5-fluorouracil, trichloroacetic acid, bleomycin, podofilox or podophyllum.

In yet another embodiment, the invention provides a method of treating HPV affected cells in a subject, comprising administering to a subject a compound or pharmaceutical composition described herein. In an aspect of the invention, the method further comprises contacting the cells with an anti-viral agent. The anti-viral agent can be, for example, an Interferon, Imiquimod, cidofovir, formaldehyde, glutaral, cimetidine, 5-fluorouracil, trichloroacetic acid, bleomycin, podofilox or podophyllum. In another aspect, the HPV can be HPV1, HPV6, HPV11, HPV16, HPV18, HPV31, HPV33, HPV35, HPV39, HPV45, HPV51, HPV52, HPV56, HPV58, HPV59, HPV66 or HPV68.

In other embodiments, the invention provides a method of treating HPV16 affected cells comprising administering to a subject a compound described herein.

In other embodiments, the invention provides a method of treating HPV16, HPV18 or HPV31 affected cells comprising administering to a subject a compound of the formula TMG-(X)$_n$-γ$^q$-(X)$_m$-A, or a pharmaceutically acceptable salt thereof, wherein m is 5, 6, 7, 8, 9, 10 or 11, n is 4, 5, 6, 7, 8, 9, 10 or 11; and the other substituents are as described above.

In other embodiments, the invention provides a method of treating HPV16, HPV18 and/or HPV31 affected cells in a subject by administering to a subject an effective amount of a compound selected from:

TMG-PyPyβPyPyβPyIm-γ$_{NH2}$-PyβPyPyβPyPyPyβPyPy-Ta;
TMG-PyPyPyβPyPyβPyIm-γ$_{NHR'}$-PyβPyPyβPyPyPyβPyβ-Ta;
TMG-PyPyPyβPyPyβPyIm-γ$_{NH2}$-PyβPyPyβPyPyPyβPyβ-Ta;
TMG-PyPyPyβPyPyβPy-γ$_{NHR'}$-PyPyPyβPyPyPyβPyβ-Ta;
TMG-PyPyPyβPyPyβPyIm-γ$_{NH2}$-PyβPyPyβPyPyPyβPyβ-Dp;
TMG-PyPyPyβPyPyβPy-γ$_{NH2}$-PyPyPyβPyPyPyβPyβ-Ta;
TMG-PyPyPyβPyPyβPy-γ$_{NH2}$-PyPyPyβPyPyPyβPyβ-Dp;
TMG-PyβPyPyImβPyPy-γ-PyβPyPyβPyPyPyβPyPyβ-Ta;
TMG-PyPyPyβPyPyβPy-γ-$_{NHR''}$-PyPyPyβPyPyPyβPyβ-Dp;
TMG-PyβPyPyImβPyPy-γ-PyβPyPyβPyPyPyβPyPyβ-Dp;
TMG-PyPyβPyPyPy-γ-PyPyβPyPyPyPyβ-Dp;
TMG-PyPyβPyPyPy-γ-PyPyβPyPyPyPyβ-Ta;
TMG-PyPyβPyPyImβPyPy-γ-PyPyβPyPyβPyPyPyβ-Ta;
TMG-PyPyβPyPyImβPyPy-γ-PyPyβPyPyPyβPyPyβ-Dp;
TMG-PyPyPyβPyPyβPyIm-γ-PyβPyPyβPyPyPyβPyβ-Ta;
TMG-PyPyPyβPyPyβPyIm-γ-PyβPyPyβPyPyPyβPyβ-Dp;
TMG-PyPyβPyPyβPyIm-γ-PyβPyPyβPyPyPyβPyβ-Dp;
TMG-PyPyβPyPyβPyIm-γ-PyβPyPyβPyPyPyβPyβ-Ta;
TMG-PyPyβPyPyβPy-γ$_{NH2}$-PyPyPyβPyPyPyβPyβ-Ta;
TMG-PyPyβPyPyβPyIm-γ$_{NH2}$-PyβPyPyβPyPyPyβPyβ-Ta;
TMG-PyPyβPyPyβPy-γ-PyPyPyβPyPyPyβPyβ-Ta;
TMG-PyPyPyβPyPyβPy-γ-PyPyPyβPyPyPyβPyβ-Ta;

or a pharmaceutically acceptable salt thereof or a mixture thereof.

In certain aspects of the embodiment, the aforementioned method further comprises administering an antiviral agent. The antiviral agent can be, for example an Interferon, Imiquimod, cidofovir, formaldehyde, glutaral, cimetidine, 5-fluorouracil, trichloroacetic acid, bleomycin, podofilox or podophyllum.

The polyamides of this invention exhibit in vitro efficacy against HPV superior to that of cidofovir or interferon for treatment of HPV-related diseases. These diseases may include genital or coetaneous warts, HPV infections of oral or genital tissues including cervical epithelia, anal cancers, neoplastic or hyper proliferative lesions caused by the HPV, conjunctiva papillomas, condyloma accumulata and recurrent respiratory papillomatosis (RRP).

DETAILED DESCRIPTION OF THE INVENTION

Abbreviations and Definitions

Figure 1:
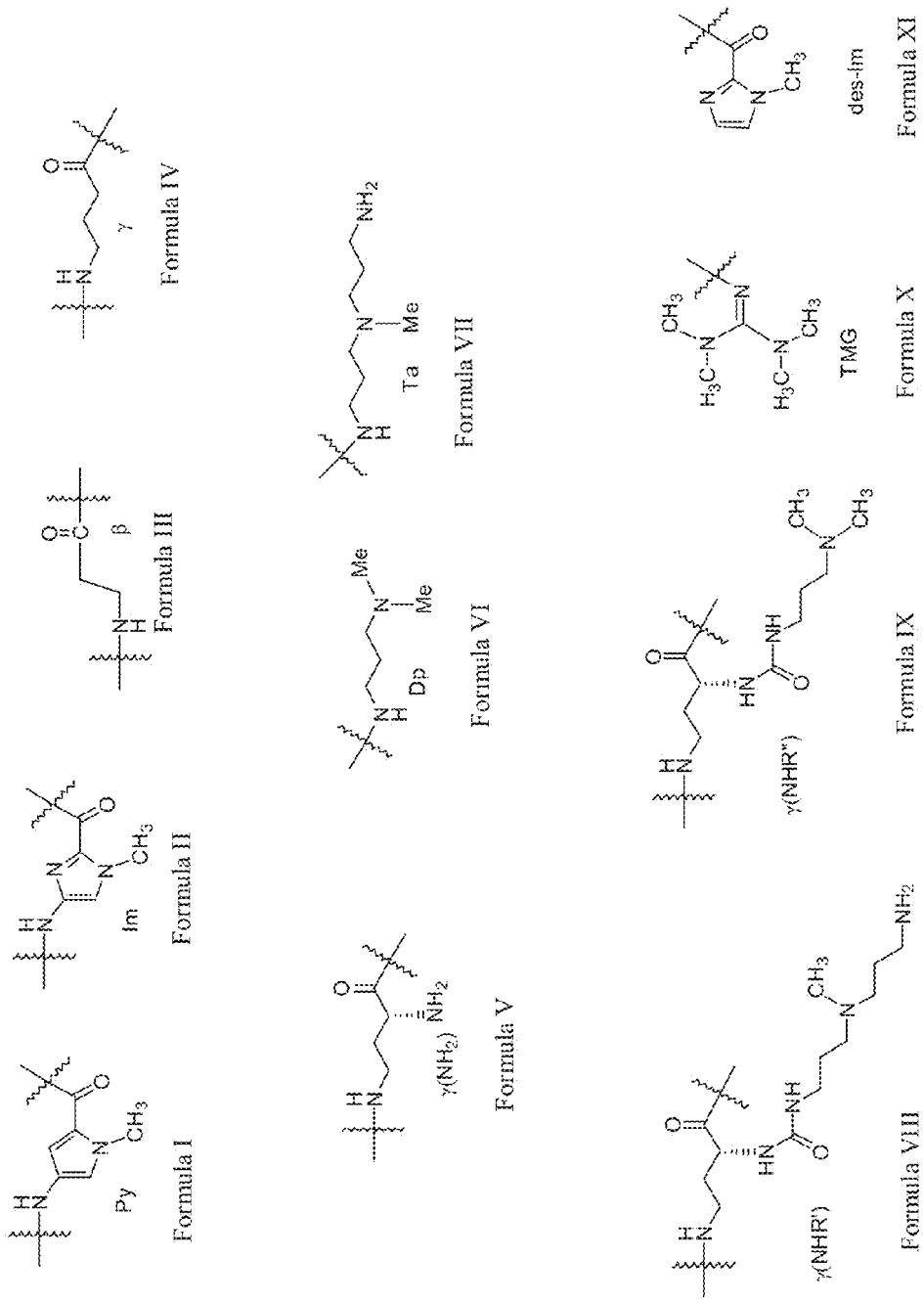
FIG. 1 illustrates the structures of various building blocks that may be present in the polyamides of the present invention.

To facilitate understanding of the invention, a number of terms and abbreviations as used herein are defined below as follows:

As used herein, the term "neoplastic cells" refer to abnormal cells that grow by cellular proliferation more rapidly than normal. As such, neoplastic cells of the invention can be cells of a benign neoplasm or can be cells of a malignant neoplasm. As used herein, the term "neoplastic disease" refers to a condition in a patient that is caused by, or associated with, the presence of neoplastic cells in the patient. Cancer is one example of a neoplastic disease. In certain aspects, the neoplastic cells are cancer cells. The cancer cells can be any type of cancer, including, for example, a carcinoma, melanoma, leukemia, sarcoma or lymphoma.

The term "carcinoma" refers to a malignant new growth made up of epithelial cells tending to infiltrate the surrounding tissues and give rise to metastases. Carcinomas which can be treated with an environmental influencer of the invention include, but are not limited to, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001.

As used herein, an effective amount is defined as the amount required to confer a therapeutic effect on the treated subject, and is typically determined based on age, surface area, weight and condition of the subject. The interrelationship of dosages for animals and humans (based on milligrams per meter squared of body surface) is described by Freireich et al., *Cancer Chemother. Rep.,* 50: 219 (1966). Body surface area may be approximately determined from height and weight of the subject. See, e.g., Scientific Tables, Geigy Pharmaceuticals, Ardsley, N.Y., 537 (1970). As used herein, "subject" refers to an animal such as a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl or 2-ethylhexyl. An alkyl group can be substituted (i.e., optionally substituted) with one or more substituents such as halo; cycloaliphatic [e.g., cycloalkyl or cycloalkenyl]; heterocycloaliphatic [e.g., heterocycloalkyl or heterocycloalkenyl]; aryl; heteroaryl; alkoxy; aroyl; heteroaroyl; acyl [e.g., (aliphatic)carbonyl, (cycloaliphatic)carbonyl, or (heterocycloaliphatic)carbonyl]; nitro; cyano; amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl]; amino [e.g., aliphaticamino, cycloaliphaticamino, or heterocycloaliphaticamino]; sulfonyl [e.g., aliphatic-S(O)$_2$—]; sulfinyl; sulfanyl; sulfoxy; urea; thiourea; sulfamoyl; sulfamide; oxo; carboxy; carbamoyl; cycloaliphaticoxy; heterocycloaliphaticoxy; aryloxy; heteroaryloxy; aralkyloxy; heteroarylalkoxy; alkoxycarbonyl; alkylcarbonyloxy; or hydroxy. Without limitation, some examples of substituted alkyls include carboxyalkyl (such as HOOC-alkyl, alkoxycarbonylalkyl, and alkylcarbonyloxyalkyl); cyanoalkyl; hydroxyalkyl; alkoxyalkyl; acylalkyl; aralkyl; (alkoxyaryl)alkyl; (sulfonylamino)alkyl (such as alkyl-S(O)$_2$-aminoalkyl); aminoalkyl; amidoalkyl; (cycloaliphatic)alkyl; or haloalkyl.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more C$_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., aliphaticcarbonyl, (cycloaliphatic)carbonyl, ((cycloaliphatic)aliphatic)carbonyl, (araliphatic)carbonyl, (heterocycloaliphatic)carbonyl, ((heterocycloaliphatic)aliphatic)carbonyl, or (heteroaraliphatic)carbonyl]; sulfonyl [e.g., aliphatic-S(O)$_2$— or amino-S(O)$_2$]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p, m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "aralkyl" group refers to an alkyl group (e.g., a C1-4 alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl]; cycloaliphatic [e.g., cycloalkyl or cycloalkenyl]; (cycloalkyl)alkyl; heterocycloalkyl; (heterocycloalkyl)alkyl; aryl; heteroaryl; alkoxy; cycloalkyloxy; heterocycloalkyloxy; aryloxy; heteroaryloxy; aralkyloxy; heteroaralkyloxy; aroyl; heteroaroyl; nitro; carboxy; alkoxycarbonyl; alkylcarbonyloxy; amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino]; cyano; halo; hydroxy; acyl; mercapto; alkylsulfanyl; sulfoxy; urea; thiourea; sulfamoyl; sulfamide; oxo; or carbamoyl.

HPV Targets

The present invention provides polyamides and analogs of polyamides that are useful for treating HPV infections and other diseases. Without wishing to be bound by any particular theory, the anti-HPV activity of the polyamides described herein provides information for predicting and developing general rules for designing polyamides against all HPV subtypes, and to other double-stranded DNA viruses. The methodology is useful in predicting which polyamide structures will possess broad-spectrum anti-viral activity against other double-stranded DNA viruses, including Epstein-Barr viruses, herpes viruses, adenoviruses, BK and pox viruses.

Time-course experiments of the anti-HPV action of the polyamides of this invention led to the discovery that certain active molecules decrease HPV DNA levels in human keratinocytes by >90% beginning at times as short as 30 min after drug treatment.

HPV DNA anchors itself to human chromosomes. The various reasons for this include a need for close proximity to human DNA replication elements for viral replication and nuclear maintenance of episomes and proper segregation of viral episomes into daughter cells during cell division. In addition, while the processes are poorly understood, viral genomes must evade innate immune systems that recognize and eliminate foreign, or non-self, DNA.

Without being bound by theory, it is possible that polyamides of the present invention are capable of either displacing the circular HPV genome from the host chromosomes resulting in their rapid loss and degradation of the episome, or that the binding of polyamides to viral or nuclear DNA activates a process resulting in specific elimination of viral rather than host DNA sequences. One possible mechanism for loss of viral DNA may include displacement of the episome from cellular chromosomes leading first to export of the HPV DNA from the host nucleus and second to rapid enzymatic degradation of the HPV DNA by nuclease enzymes. An additional conclusion is that a major reason for tethering of HPV DNA to host chromosomes is to protect the viral DNA from this degradative pathway. Alternatively, the polyamides may alter the physical properties of episomal DNA in the nucleus resulting in recognition and elimination of the foreign DNA by host defense mechanisms. These predictions can be extended to other drugs that bind to the DNA minor groove, and they can be extended to other double-stranded DNA viruses, including Epstein Barr viruses, that employ similar or related strategies for episomal maintenance.

Thus, these molecules may be useful for binding double-stranded DNA in a sequence-specific manner, comprising contacting a DNA-target sequence within said DNA with a DNA-binding compound described herein, in conditions allowing the binding to occur. This may be carried out in vivo, in vitro or ex vivo. Further, the method may be carried out in a cell, and the double stranded DNA may be endogenous or heterologous to the cell.

Polyamide binding affinity and sequence specificity may be determined via qualitative and quantitative footprint titration experiments known in the art (see Brenowitz, M.; Senear, D. F.; Shea, M. A.; Ackers, G. K. *Methods Enzymol.* 1986, 130, 132; Mitra, S.; Shcherbakova, I. V.; Altman, R. B.; Brenowitz, M.; Laederach, A. *Nucl. Acids Res.* 2008, 36, e63; White, S.; Baird, E. E.; Dervan, P. B. *Biochemistry* 1996, 35, 12532; and White, S.; Baird, E. E.; Dervan, P. B. Chemistry & Biology 1997, 4, 569.)

Polyamides of the present invention may useful for detecting the presence of double stranded DNA of a specific sequence for diagnostic or preparative purposes. The sample containing the double stranded DNA may be contacted by polyamide linked to a solid substrate, thereby isolating DNA comprising a desired sequence. Alternatively, polyamides linked to a suitable detectable marker, such as biotin, a hapten, a radioisotope or a dye molecule, can be contacted by a sample containing double stranded DNA.

Furthermore, these molecules may be utilized in a method of reducing or inhibiting proliferation of neoplastic cells, comprising contacting the cells with an effective amount of a compound described herein. The contacting of the cells with the agents of the invention results in an interference with the expression of genes associated with neoplastic cells. The agent binds to the DNA sequence encoding the gene, thereby reducing or inhibiting expression of the gene.

In some embodiments of the method, the neoplastic cells may be cancer cells. The cells may include colon carcinoma cells, hepatocellular carcinoma cells, cervical carcinoma cells, lung epidermocarcinoma cells, mammary gland adenocarcinoma cells, pancreatic carcinoma cells, prostatic carcinoma cells, osteosarcoma cells, melanoma cells, acute promyelocytic leukemia cells, acute lymphoblastic leukemia cells, hepatocancreatico adenocarcinoma cells and Burkitt's lymphoma B cells. Efficacy is identified by detecting that signs or symptoms associated with the neoplastic disease are lessened. The signs and symptoms characteristic of particular types of neoplastic disease are well known to the skilled clinician, as are methods for monitoring the signs and conditions. For example, imaging methods can be used to determine that a tumor has decreased in size, or is increasing in size at a lower rate, due to treatment according to the present methods.

Additionally, these molecules may be useful in a method of treating virus infected cells comprising contacting the cells with an effective amount of a compound described herein. The methods may be useful for treating other infections caused by a double-stranded DNA virus.

In the case of HPV, it is known that tethering to the chromosomes occurs though long sequences of DNA bases A and T. These AT tracts are targets for pyrrole-containing polyamides, because of recognition of AT base pairs by pyrrole as found in the natural product Distamycin, which can be considered a partial progenitor of polyamide structure used for DNA binding. Distamycin binds to AT-rich DNA, but it is a small enough molecule that very long AT tracts are not necessary to attract Distamycin: AT-regions only five bases long are sufficient for recognition by Distamycin.

AT-rich regions of DNA in so-called "fragile DNA" are apparent targets of Distamycin, and are expressed by cells in response to Distamycin treatment. Furthermore, in model systems of DNA rearrangement and processing, such as found in ciliates and other microorganisms, it is AT-rich regions that are targeted for elimination during genomic rearrangements, suggesting that cells may retain an evolutionarily conserved mechanism for processing and elimination of DNA, and that the AT-rich sequences involved are likely targets for binding by pyrroles of naturally occurring or synthetic polyamides.

From the inventions described here, one can develop useful drugs against DNA viruses such as the HPV subtypes by considering the so-called selectivity index (SI: ratio of $IC_{50}$ to $TD_{50}$) and routine experimentation to determine an optimal range of selectivity indices. Distamycin itself is too toxic for most or all applications as an anti-viral, while our designed and purpose-built polyamides that target AT-rich DNA regions generally have very low toxicity and very high SI in cell culture.

In some embodiments, polyamide sequences exhibiting anti-HPV activity with the HPV types, especially, HPV 1, 6, 11, 16, 18 and 31, display the ability to displace or eliminate HPV DNA from host chromosomes, which can result in broad applicability against HPVs. These include HPV11, which is responsible, in part, for the frequently fatal disease known as respiratory papillomatosis, as well as genital warts, HPV1 and 6, which cause common warts and warts of the external genitalia, anus and cervix, respectively, and HPV16, 18 and 31, which are responsible for anal and/or cervical cancers.

Chemical Background

Certain oligomers of nitrogen heterocycles can be used to bind to particular regions of double stranded DNA. Particularly, N-methyl imidazole (I), des-amino-N-methyl imidazole (Im), and N-methylpyrrole (P) have a specific affinity for particular bases. This specificity can be modified based upon the order in which these compounds are linked. It has been shown that there is specificity in that G/C is complemented by Im/P or I/P, C/G is complemented by P/Im or P/I, and A/T and T/A are redundantly complemented by P/P.

In effect, N-methyl imidazole and des-amino-N-methyl imidazole tend to be associated with guanine, while N-methylpyrrole is associated with cytosine, adenine and thymine. By providing for two chains of the heterocycles, as 1 or 2 molecules, a 2:1 complex with double stranded DNA is formed, with the two chains; of the oligomer antiparallel, where G/C pairs have Im/P or I/P in juxtaposition, C/G pairs have P/Im or P/I, and T/A pairs have P/P in juxtaposition. The heterocycle oligomers are joined by amide (carbamyl) groups, where the NH may participate in hydrogen bonding with nitrogen unpaired electrons, particularly of adenine.

Polyamides may be synthesized to form hairpin compounds by incorporating compounds, such as gamma-aminobutyric acid (.gamma.) or gamma-amino-beta-aminobutyric acid (.gamma NH.sub.2), to allow a single polyamide to form a complex with DNA. Such a structure has been found to significantly increase the binding affinity of the polyamide to a target sequence of DNA.

Beta-alanine (.beta.) may be substituted for a pair of N-methylpyrrole groups when an AT or TA base pair is the target sequence. The added flexibility of the beta-alanine can help the entire polyamide stay "in register" with the target sequence of DNA.

In some embodiments, the polyamide molecule begins with des-amino-N-methyl imidazole that has a specific affinity for guanosine. In other embodiments, the polyamide molecule ends with either 3-(Dimethylamino) propylamine (Dp) or 3,3'-Diamino-N-methyldipropylamine (Ta). Dye molecules can be incorporated at the amino groups of the .gamma.-amino-butyric acid, the Ta, or at both of these sites if both are available in the same molecule.

More recently it has been discovered that the inclusion of a new aromatic amino acid, 3-hydroxy-N-methylpyrrole (Hp), when incorporated into a polyamide and paired opposite Py, provides the means to discriminate A-T from T-A. White S., et al., Nature 391, 436-38 (1998). Unexpectedly, the replacement of a single hydrogen atom on the pyrrole with a hydroxy group in an Hp/P pair regulates the affinity and the specificity of a polyamide by an order of magnitude. Using Hp together with P and Im or I in polyamides to form six aromatic amino acid pairs (I/P, Im/P, P/Im, P/I, Hp/P and P/Hp) provides a code to distinguish all four Watson-Crick base pairs in the minor groove of DNA in environments in which Hp does not decompose.

Naturally occurring pyrrole-containing polyamides such as distamycin and netropsin, as well as their pyrrole/imidazole-containing synthetic analogs, bind with high affinity to the minor groove of DNA. Direct evidence of specific polyamide-DNA binding has been extensively reported by the Dervan group using X-ray crystallography, NMR structure determinations and quantitative affinity cleavage methods (Baird and Dervan, 1998; Pilch et al., *Biochemistry*, 38, 2143-51, 1999; Pilch et al., *Proc. Natl. Acad. Sci. USA*, 93, 8306-11 1996; Wang, Ellervik, and Dervan, *Bioorg. Med. Chem.*, 9, 653-7, 2001; White, Baird, and Dervan, *Biochemistry*, 35, 12532-27, 1996; White, Baird, and Dervan, *Chem. Biol.*, 4, 569-78, 1997, all of which are incorporated herein by reference). Because of the H-bonding scheme, synthetic polyamides can be designed to recognize specific DNA sequences.

The rules for DNA recognition by polyamides are summarized in the following paragraphs (White, Baird, and Dervan, *Chem. Biol.*, 4, 569-78, 1997). Pyrrole (typically abbreviated Py or P,) binds to the three nucleotides that present hydrogen bond acceptors in the minor groove, or A, T and C (Kielkopf et al., *Science*, 282, 111-5, 1998; Kielkopf, et al., *Nat. Struct. Biol.*, 5, 104-9, 1998; Melander, Herman, and Dervan, *Chemistry*, 6, 4487-97, 2000, all of which are incorporated herein by reference). These nucleotides present only hydrogen bond acceptors to the minor groove: A and C each offer one lone pair of electrons while T offers two lone pairs from the carbonyl oxygen bound to C2. It is the amide NH of the hairpin pyrrole amino acids that is the hydrogen bond donor. So, the pyrrole ring acts as a curved spacer that presents amide NHs at the correct distance and curvature to match up with the pattern of hydrogen bond acceptors presented by A, C and T when located in B-form DNA. Imidazole (Structure II below) is typically abbreviated I.

Polyamides

General Structure

A polyamide of the invention may be generally characterized as a polymeric or oligomeric molecule containing a plurality of carboxamide repeating units as well as one or more guanidinyl radicals, which may be at one or both ends of the molecule and/or along the backbone of the polyamide. The polyamide may be a compound having a polyamide backbone containing an interior unit selected from γ-aminobutyric acid (γ); 2,4-diaminobutyric acid ($\gamma_{NH2}$), which may be either the (R) or (s) isomer and which may be linked in to the polyamide backbone through either the 2-amino group or the 4-amino group; or $H_2N(CH_2)_2CH(NHC(=O)$ NHR)CO$_2$H, wherein R is —(CH$_2$)$_3$—N(CH$_3$)—(CH$_2$)$_3$—NH$_2$ ($\gamma_{NHR'}$) or —(CH$_2$)$_3$—N(CH$_3$)$_2$ ($\gamma_{NHR''}$), each of which may be either the (R) or (S) isomer, and at least one guanidinyl radical pendant to 2,4-diaminobutyric acid ($\gamma_{NH2}$), pendant to H$_2$N(CH$_2$)$_2$CH(NHC(=O)NHR)CO$_2$H, wherein R is —(CH$_2$)$_3$—N(CH$_3$)—(CH$_2$)$_3$—NH$_2$ ($\gamma_{NHR'}$), or at a terminal position of the polyamide backbone. The compound may be a pharmaceutically acceptable salt of such a polyamide. In the context of this invention, "interior" means at a position along the polymer backbone other than the terminal (end) positions or a position immediately adjacent to a terminal position. The polyamide backbone may contain a plurality of units (for example, 5 to 30, or 7 to 28, or 9 to 24, or 11 to 22 or 15 to 21 or 16 to 21 units) selected from the group consisting of 4-amino-2-carbonyl-N-methylimidazole (Im), 4-amino-2-carbonyl-N-methylpyrrole (Py) and β-alanine (B). Typically, the polyamide has a number average molecular weight of from about 1000 to about 2900 or from about 1200 to about 2700.

In one aspect of the invention, the guanidinyl radical is connected to a terminal 4-amino-2-carbonyl-N-methylpyrrole (Py) unit. The guanidinyl radical may be unsubstituted (GUAN) or substituted. That is, any or each of the three nitrogen atoms present in the guanidinyl radical may bear substituents other than hydrogen. Such substituents may be, for example, alkyl, aralkyl and/or aryl groups. In one embodiment of the invention, two of the nitrogen atoms each bear two alkyl groups, such as C1-C4 alkyl groups. For example, the guanidinyl radical may be tetramethylguanidinyl (TMG).

The compound may contain an end group selected from 3,3'-diamino-N-methyldipropylamine (Ta) or 3-(dimethylamino)propylamine (Dp). The primary amine group of the Ta end group may be reacted to provide a guanidinyl radical. That is, the C terminus of the polyamide may be terminated with a guanidinyl radical such as tetramethylguanidinyl (TMG).

The structures of certain polyamide compounds in accordance with the present invention may be described by the formula:

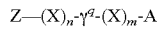

or a pharmaceutically acceptable salt thereof, wherein
  m is 3-16 (or 4-15, or 5-14, or 6-13 or 7-12);
  n is 2-14 (or 3-13, or 3-12, or 4-12, or 4-10);
  Z is guanidinylated 4-amino-2-carbonyl-N-methylpyrrole, N-formylated 4-amino-2-carbonyl-N-methylpyrrole, N-acetylated 4-amino-2-carbonyl-N-methylpyrrole, or des-aminoimidazole (des-Im, Formula XI, FIG. 1);
  each X is independently selected from 4-amino-2-carbonyl-N-methylimidazole (Im, Formula II, FIG. 1), 4-amino-2-carbonyl-N-methylpyrrole (Py, Formula I, FIG. 1) or β-alanine (β, Formula III, FIG. 1);
  $\gamma^q$ is γ-aminobutyric acid (γ, Formula IV, FIG. 1); 2,4-diaminobutyric acid ($\gamma_{NH2}$, corresponding to Formula V in FIG. 1 when the 2,4-diaminobutyric acid is the (R) isomer and linkage into the polyamide takes place through the γ amino group); guanidinylated 2,4-diaminobutyric acid; or H$_2$N(CH$_2$)$_2$CH(NHC(=O)NHR)CO$_2$H, wherein R is —(CH$_2$)$_3$—N(CH$_3$)—(CH$_2$)$_3$—NH$_2$ ($\gamma_{NHR'}$, Formula VIII, FIG. 1), guanidinylated —(CH$_2$)$_3$—N(CH$_3$)—(CH$_2$)$_3$—NH$_2$, or —(CH$_2$)$_3$—N(CH$_3$)$_2$ ($\gamma_{NHR''}$, Formula IX, FIG. 1);
  A is 3,3'-diamino-N-methyldipropylamine (Ta, Formula VII, FIG. 1), guanidinylated 3,3'-diamino-N-methyldipropylamine; or 3-(dimethylamino)propylamine (Dp, Formula VI, FIG. 1);

wherein the compound contains at least one primary amine group, which has been guanidinylated.

In such compounds, at least one primary amine group (—NH$_2$) present initially in a precursor to the compound has been converted to a guanidinyl group (radical). For example, the primary amine group of a 4-amino-2-carbonyl-N-methylpyrrole N-terminus end group, a 3-(dimethylamino)propylamine C-terminus end group, or a —(CH$_2$)$_3$—N(CH$_3$)—(CH$_2$)$_3$—NH$_2$ group present in the building block $\gamma_{NHR'}$ may be guanidinylated.

The structures of other particular polyamide compounds according to one aspect of the invention are described, with the restrictions and definitions given below, by the formula:
  G-(X)$_n$-$\gamma^q$-(X)$_m$-A.

In such polyamide compounds, the polyamide molecule begins with a guanidinyl radical, such as a tetramethylguanidinyl (TMG, Formula X) radical. The guanidinyl radical may correspond to the structural formulae —N=C(NR$^1$R$^2$)(NR$^3$R$^4$) and/or —NR$^5$—C(NR$^1$R$^2$)(=NR$^3$), wherein R$^{1-5}$ are the same or different and may be selected from H, alkyl (e.g., C1-C4 alkyl, such as methyl, ethyl, propyl, isopropyl, n-butyl, isobutyl and the like), aryl (phenyl, pyridyl, imidazolyl) and other 5- or 6-membered ring aryl or heteroaryl groups, aralkyl (e.g., benzyl) and their variously substituted derivatives) or a pharmaceutically acceptable salt thereof (e.g., the guanidinyl radical may be in the form of a guanidinium species). Various types of suitable guanidinyl radicals, including their tautomers, are illustrated in FIGS. 8A and 8B.

One aspect of the invention employs a tetramethylguanidinyl radical at the N-terminus of the polyamide (TMG, Formula X). This tetramethylguanidinyl radical is attached to the polyamide via a carbon-nitrogen double bond (imine) linkage. For example, where the unit adjacent to the TMG radical is 4-amino-2-carbonyl-N-methylpyrrole (Py), the 4-amino group of the 4-amino-2-carbonyl-N-methylpyrrole provides the nitrogen atom involved in the imine linkage.

In other aspects of the invention, the guanidinyl radical may be unsubstituted (GUAN), monosubstituted, N,N'-disubstituted, gem-disubstituted, N,N,N'-trisubstituted, or N,N,N',N'-tetrasubstituted. The unsubstituted, monosubstituted, disubstituted, and trisubstituted guanidinyl radicals exist as tautomers; such tautomers are shown in FIGS. 8A and 8B. As illustrated in FIGS. 8A and 8B, the position of the carbon-nitrogen double bond (imine) may vary.

Figure 8A:
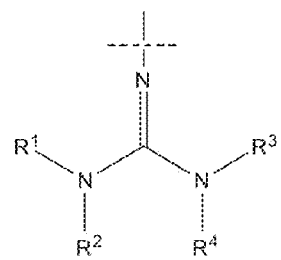
FIGS. 8A and 8B illustrate various types of guanidinyl radicals, including different substitution patterns and tautomers, which may be present in the polyamides of the present invention.
Figure 8A:
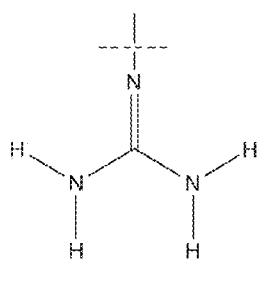
Figure 8A:
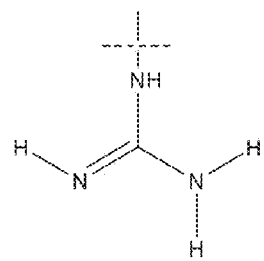
Figure 8A:
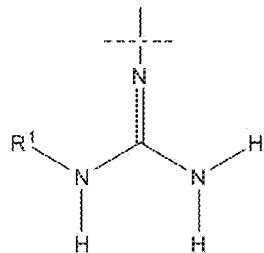
Figure 8A:
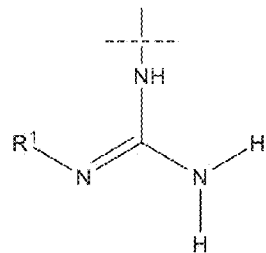
Figure 8A:
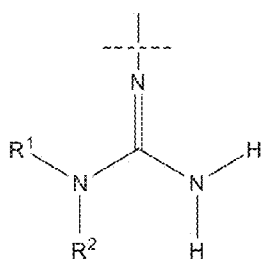
Figure 8A:
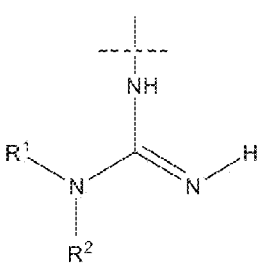
Figure 8B:
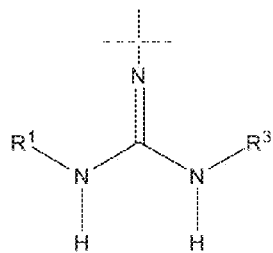
Figure 8B:
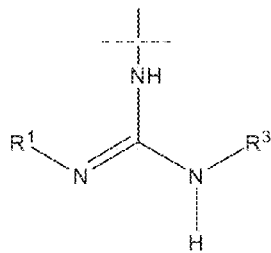
Figure 8B:
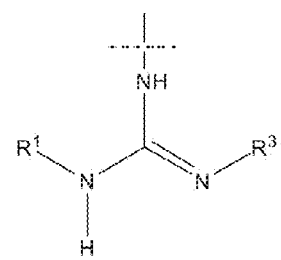
Figure 8B:
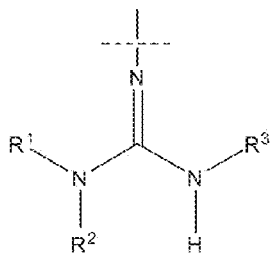
Figure 8B:
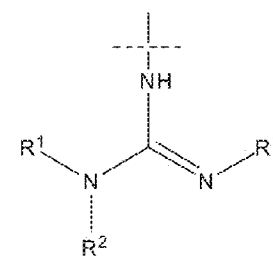
Figure 8B:
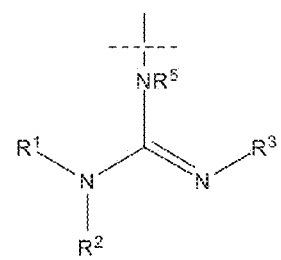
Figure 8B:
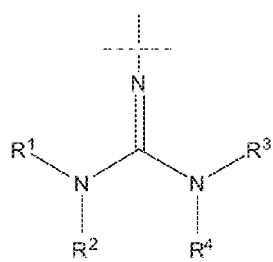
Figure 9:
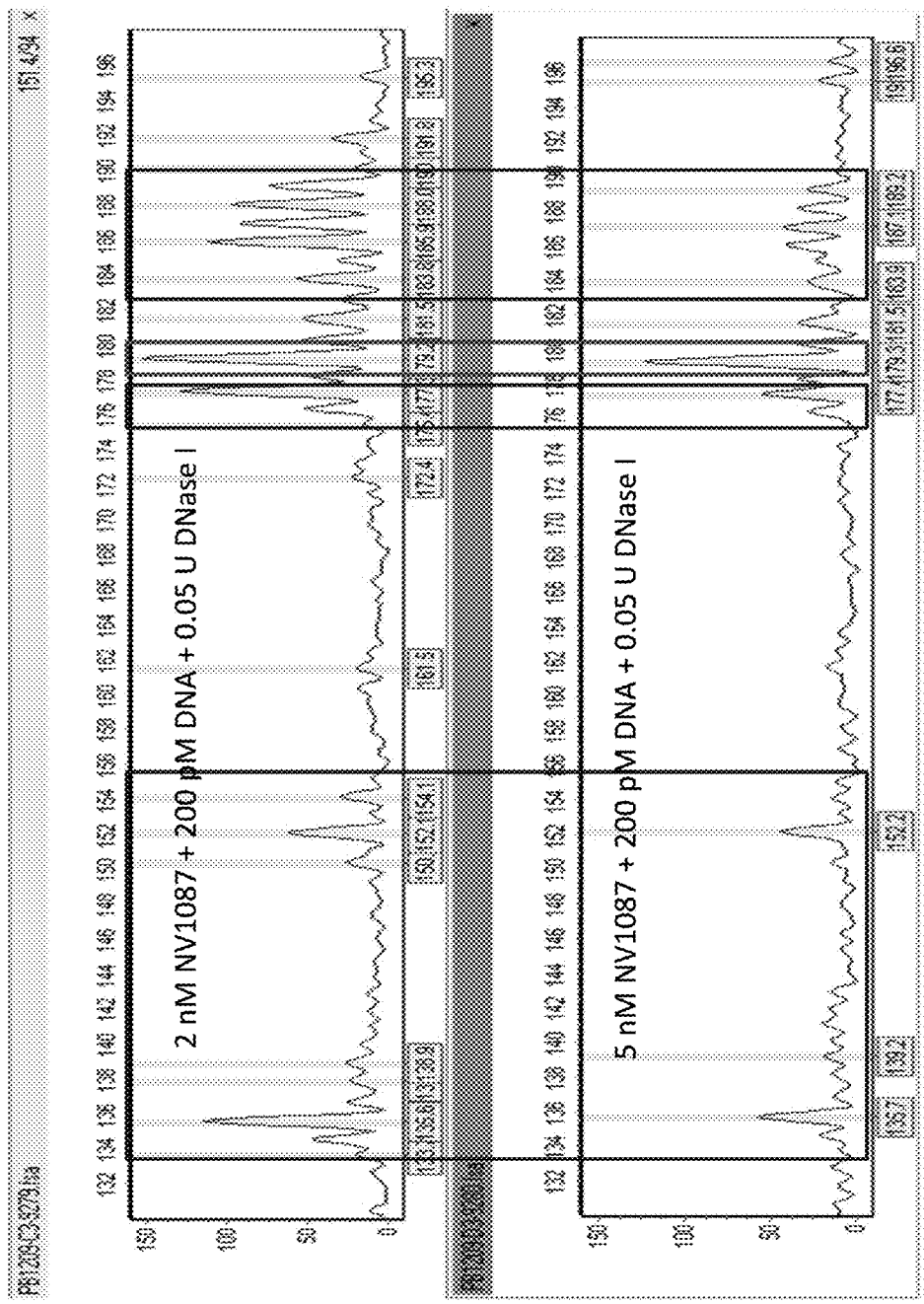
FIG. 9 illustrates a footprinting experiment of NV1087 on a sequence of HPV16 (365 bp: 7662-122). All reactions were carried out in presence of DMSO and CHAPS, and the final DNA concentration was 200 pM. The polyamide concentration varied (2 nM and 5 nM). Reactions were incubated with polyamide at 37° C. for 5-6 hrs. The decrease in peak heights relative to the reference peak is interpreted to mean that increasing polyamide concentration protects the DNA from digestion by DNase I.

An extensive, but not exhaustive, set of substitution patterns and related tautomers for the guanidinyl radical are shown in FIGS. 8A and 8B. Any H may independently be substituted with groups R$^{1-5}$ (independently selected from alkyl, aryl, aralkyl) In each of the guanidinyl radical structures shown in FIGS. 8A and 8B, the horizontal dotted line indicates that the guanidinyl radical is bonded to a polyamide via the bond that bears the horizontal dotted line. It is to be understood that the guanidinyl-substituted compounds of the invention may exhibit tautomerism of the sort described above. It is also to be understood that the present invention encompasses all tautomeric forms of the variously substituted guanidinyl-substituted polyamides, and mixtures thereof, and is not to be limited to any one tautomeric form described within the formal drawings.

As isolated by crystallization and/or HPLC in 0.1% TFA and as used in contact with cells, tissue culture, or subjects, the highly basic nature of guanidines will generally cause them to be present as acid addition salts, i.e. in their protonated form. All pharmaceutically acceptable salts of all tautomers described herein are part of the present invention.

A polyamide molecule corresponding to the formula G-(X)$_n$-γ$^q$-(X)$_m$-A may end with either 3-(dimethylamino)propylamine (Dp, Formula VI) or 3,3'-diamino-N-methyldipropylamine (Ta, Formula VII). That is, in certain embodiments of the invention a guanidinyl (G) radical is present at the N terminus of the polyamide molecule and a Dp or Ta unit or other terminating group ("A" in the above-mentioned formula) is present at the C terminus of the molecule. All γ$^q$ unit appears at an interior position within the polyamide backbone, being separated from the G unit by the structural sequence —(X)$_n$— and being separated from the A unit (Dp or Ta) by the structural sequence —(X)$_m$—. The γ$^q$ unit may provide a hairpin turn in the polyamide compound. Structural sequences —(X)$_m$— and —(X)$_n$— are comprised of multiple linked units X selected from the group consisting of 4-amino-2-carbonyl-N-methylimidazole (Im, Formula II), 4-amino-2-carbonyl-N-methylpyrrole (Py, Formula I), and β-alanine (β, Formula III).

Structures of the units TMG, X, γ$^q$ and A are shown in FIG. 1. The terms in the above-mentioned formula for the polyamide compounds of the invention are defined as follows.

TMG may be the N-terminal capping group and is tetramethylguanidinyl (Formula X). If the guanidinyl radical is not located at the N-terminus, the N-terminal capping group may be des-Im, or des-aminoimidazole, as shown in Formula XI, FIG. 1.

X is a unit obtained by condensation of one or more polyamide building blocks that include the 4-amino-2-carboxylic acid derivative of N-methylpyrrole (providing unit Py, Formula I), beta-alanine (providing unit β, Formula III), and the 4-amino-2-carboxylic acid derivative of N-methylimidazole (providing unit Im, Formula II).

γ$^q$ can be a unit obtained by condensation of a gamma-aminobutyric acid building block (providing unit γ, Formula IV), the chiral analogs of gamma-aminobutyric acid known as (R)-2,4-diaminobutyric acid and (S)-2,4-diaminobutyric acid (providing unit γ$_{NH2}$, corresponding to Formula V when the (R) isomer is employed and the amine group in the 4 (γ) position has been reacted into the polyamide polymer backbone), and H$_2$N(CH$_2$)$_2$CH(NHC(=O)NHR)CO$_2$H, wherein R is —(CH$_2$)$_3$—N(CH$_3$)—(CH$_2$)$_3$—NH$_2$ (γ$_{NHR'}$, Formula VIII) or —(CH$_2$)$_3$—N(CH$_3$)$_2$ (γ$_{NHR''}$, Formula IX). The latter two units may also be formed by reaction of an amino group of 2,4-diaminobutyric acid following incorporation of such compound into the polyamide with a suitable reactant or reactants. For example, γ$_{NHR'}$ (Formula VIII) may result from (R)-2,4-diaminobutyric acid which has formed a urea with Ta (3,3'-diamino-N-methyldipropylamine). The unit γ$_{NHR''}$ (Formula IX) may result from (R)-2,4-diaminobutyric acid which has formed a urea with Dp (3-(dimethylamino)propylamine). These units (γ$_{NHR'}$, γ$_{NHR''}$) may have either (R) or (S) stereochemistry. A 2,4-diaminobutyric acid building block may be incorporated into the polyamide by reaction (condensation) of the amine group at the 2 (a) position, providing an alpha turn, or at the 4 (γ) position, providing a gamma turn. In the context of this invention, "2,4-diaminobutyric acid" includes the (S) as well as the (R) isomer.

A may be a unit obtained by condensation of 3-(dimethylamino)propylamine (providing unit Dp, Formula VI) or 3,3'-diamino-N-methyldipropylamine (providing unit Ta, Formula VII).

In certain embodiments of the invention, a β-alanine unit occurs after one, two, three or four contiguous Py and/or Im building blocks as exemplified by -Py-β, -Py-Py-β, -Py-Py-Py-β and -Im-Py-Py-β. The polyamide may contain, for example, 2 to 7 or 3 to 6β units per molecule. In various embodiments of the invention, the structural sequence —(X)$_m$— may contain 2 to 5β units. In other embodiments, the structural sequence —(X)$_n$— may contain 1 to 3β units.

In certain embodiments of the invention, the polyamide contains 0, 1 or 2 Im units per molecule.

Polyamides of the invention include the exemplary compounds:
TMG-PyPyβPyPyβPyIm-γ$_{NH2}$-PyβPyPyβPyPyPyβPyPy-Ta;
TMG-PyPyPyβPyPyβPyIm-γ$_{NHR'}$-PyβPyPyβPyPyPyβPyβ-Ta;
TMG-PyPyPyβPyPyβPyIm-γ$_{NH2}$-PyβPyPyβPyPyPyβPyβ-Ta;
TMG-PyPyPyβPyPyβPy-γ$_{NHR'}$-PyPyPyβPyPyPyβPyβ-Ta;
TMG-PyPyPyβPyPyβPyIm-γ$_{NH2}$-PyβPyPyβPyPyPyβPyβ-Dp;
TMG-PyPyPyβPyPyβPy-γ$_{NH2}$-PyPyPyβPyPyPyβPyβ-Ta;
TMG-PyPyPyβPyPyβPy-γ$_{NH2}$-PyPyPyβPyPyPyβPyβ-Dp;
TMG-PyβPyPyImβPyPyγPyPyβPyPyPyβPyPyPyβ-Ta;
TMG-PyPyPyβPyPyβPy-γ$_{NHR''}$-PyPyPyβPyPyPyβPyβ-Dp;
TMG-PyβPyPyImβPyPy-γ-PyPyβPyPyPyβPyPyPyβ-Dp;
TMG-PyβPyPyPy-γ-PyPyβPyPyPyPyγ-Dp;
TMG-PyβPyPyPy-γ-PyPyβPyPyPyPyγ-Ta;
TMG-PyPyβPyPyPy-γ-PyPyβPyPyPyPyβ-Dp;
TMG-PyPyβPyPyPy-γ-PyPyβPyPyPyPyβ-Ta;
TMG-PyPyβPyPyImβPyPy-γ-PyPyβPyPyPyβPyPyPyβ-Ta;
TMG-PyPyβPyPyImβPyPy-γ-PyPyβPyPyPyβPyPyPyβ-Dp;
TMG-PyPyβPyPyPyβPyIm-γ-PyβPyPyβPyPyPyβPyβ-Ta;
TMG-PyPyβPyPyPyβPyIm-γ-PyβPyPyβPyPyPyβPyβ-Dp;
TMG-PyPyPyPyβPyIm-γ-PyβPyPyβPyPyPyβPyβ-Dp;
TMG-PyPyPyPyβPyIm-γ-PyβPyPyβPyPyPyβPyβ-Ta;
TMG-PyImβPyPy-γ-PyPyPyβPyPyPyβ-Ta;
TMG-PyPyβPyPyβPy-γ$_{NH2}$-PyPyPyβPyPyPyβPyβ-Ta;
TMG-PyPyβPyPyβPyIm-γ$_{NH2}$-PyβPyPyβPyPyPyβPyβ-Ta;
TMG-PyPyβPyPyβPy-γ-PyPyPyβPyPyPyβPyβ-Ta;
TMG-PyPyβPyPyβPy-γ-PyPyPyβPyPyPyβPyβ-Ta;
TMG-PyImPyIm-γ-PyPyPyPyβ-Ta;
TMG-PyImβIm-γ-PyβPyPyβ-Ta;
TMG-PyImPyIm-γ-PyβPyPyβ-Ta;
TMG-PyImβIm-γ-PyPyPyβ-Ta;
GUAN-PyImβIm-γ-PyβPyPyβ-Ta;
and pharmaceutically acceptable salts thereof.

In yet other embodiments, the polyamides contain, at the C-terminal end, FAM (5-Carboxyfluorescein), BIODIPY or another compound that can be used to determine cellular localization. In some embodiments, polyamides containing FITC at the C-terminal end are more readily taken up by cells. An example of fluorescent labeled polyamides of the invention include the exemplary compounds:
TMG-PyPyPyβPyPyβPyIm-γ-PyβPyPyβPyPyPyβPyβ-Ta-FAM;
wherein FAM represents 5-Carboxyfluorescein.

In even other embodiments, the polyamides target HPV1, HPV6, HPV11, HPV18, HPV16, HPV31, HPV33, HPV35, HPV39, HPV45, HPV51, HPV52, HPV56, HPV58, HPV59, HPV66 or HPV68.

In further embodiments, the polyamides target DNA viruses, which include Epstein-Barr virus, herpes virus, pox viruses and other double-stranded DNA viruses. Possible targets within these viruses may include sequences required for tethering, maintenance, or replication.

General Synthetic Schemes

The polyamides as described herein may be produced from known starting materials using conventional methods. See for example WO 05/033282, Belitsky et al., (2002) *Bioorg. Med. Chem.*, 10, 2767-74; Zhang, et al. (2006) *J. Am. Chem. Soc.*

128:8766-76; Turner, et al. (2001) *Organic Letters*, 3:1201-03, all of which are incorporated herein by reference.

Polyamides can be prepared using manual solid-phase synthesis as well as automated solid-phase chemistry. Each coupling may be followed by HPLC and HPLC/mass spectrometry.

In solution-phase polyamide synthesis, two main amide bond forming routes may be used: (1) the haloform reaction and (2) reactions of amines with acids in the presence of coupling agents like DCC, EDC, PyβOP or HATU (when required). For the heterocyclic building blocks utilized in the present invention, the haloform reaction can be the method described in Xiao et al., (2000) *Chin. J. Chem.*, 18:603-07 and Xiao et al., (2000) *J. Org. Chem.*, 65:5506-13, both of which are incorporated herein by reference in their entirety for all purposes.

The steps in the haloform reaction yielding a nitro-substituted heterocycle could, for example, be followed by reduction of the nitro group with $H_2$ and Pd/C. The resulting free amino group can be protected or immediately coupled to an additional building block. Common building blocks can be identified for a polyamide, allowing efficient solution phase synthesis: the Py-Py dimer can be made and purified on a large scale and then used directly or elaborated further to form the major sections of the target sequence, and then the final product.

Yet another method of synthesis is to prepare a polyamide oligomer starting with Boc-β-alanine-PAM solid phase synthesis resin, or a similar commercially available resin, adding building blocks as required for the target sequence.

The guanidinyl radicals in the compounds may be introduced by any suitable method, including for example the conversion of a primary amine group on a terminal Py unit, a Ta end group, a $H_2N(CH_2)_2CH(NHC(=O)NHR)CO_2H$ unit, wherein R is $—(CH_2)_3—N(CH_3)—(CH_2)_3—NH_2$ ($\gamma_{NHR'}$), or a 2,4-diaminobutyric acid ($\gamma_{NH2}$) unit. Synthetic methods for reacting primary amines to form guanidinyls are well known in the art. Examples of such methods include the reaction of amines with S-methyl isothiouronium salts (the Rathke guanidine synthesis), O-methylisouronium salts and chloroformamidinium (Vilsmeier) salts.

Figure 3:
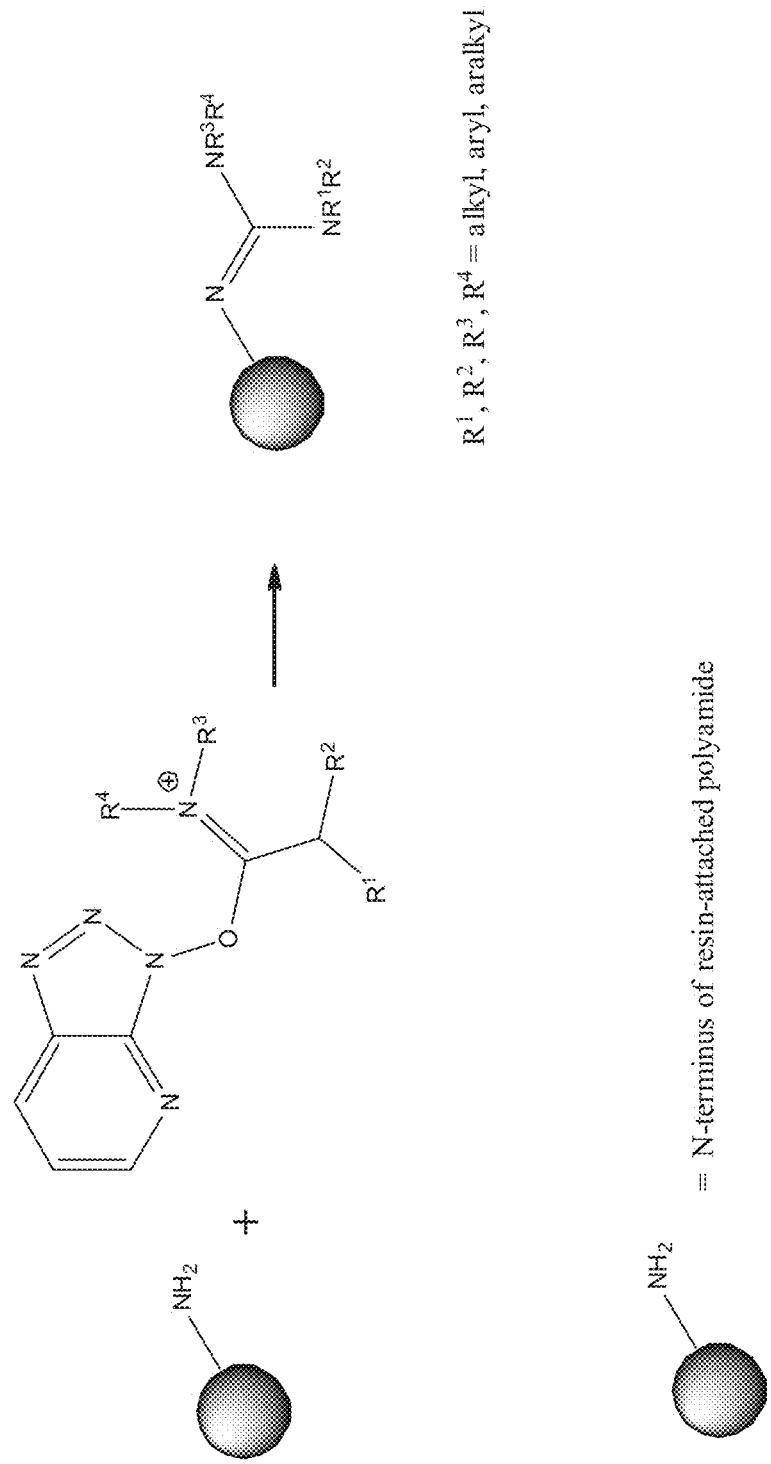
FIG. 3 illustrates a synthetic route that may be employed to provide a guanidinylated polyamide in accordance with the invention wherein the guanidinyl radical is tetrasubstituted.

A tetrasubstituted guanidinyl radical [$—N=C(NR_2)_2$, where the R groups may be the same or different and may be, e.g., alkyl, aralkyl or aryl] may be introduced on the N-terminus of a polyamide by treating a deprotected, resin-attached polyamide containing a primary amine group with a tetrasubstituted uronium reactant such as HATU [2-(7-aza-1H-benzotriazole-1-yl)-1,1,3,3-tetramethyluronium hexyluorophosphate]. FIG. 3 illustrates this synthetic route. Tetrasubstituted guanidinyl radicals exist only in the form shown in this paragraph. All guanidinyl radicals wherein at least one R is hydrogen can exist in a variety of tautomeric forms, as depicted in FIGS. 8A and 8B. This invention includes all possible tautomeric forms and salts thereof (including acid addition salts) of the various guanidinyl radicals described herein.

Figure 4:
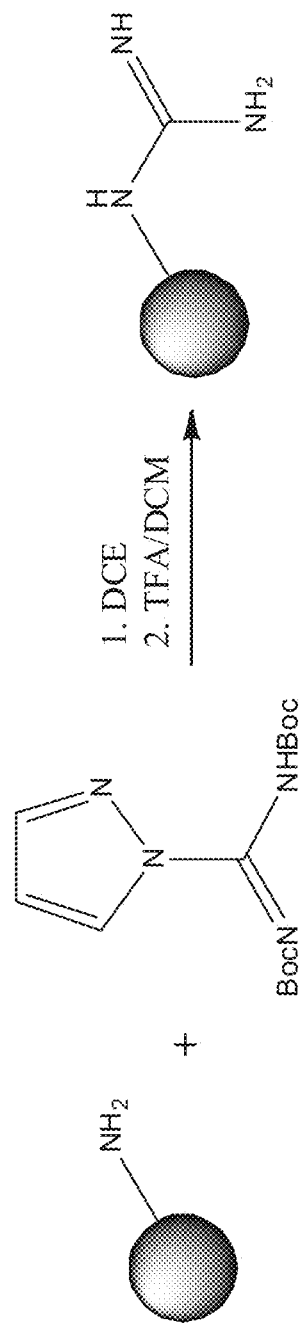
FIG. 4 illustrates a synthetic route which may be employed to provide a guanidinylated polyamide in accordance with the invention wherein the guanidinyl radical is unsubstituted (i.e., the nitrogen atoms in the guanidinyl radical do not bear any substituents other than hydrogen).

An unsubstituted guanidinyl radical [$—NH—C(=NH)NH_2$ or tautomer thereof] may be introduced on the N-terminus of a polyamide by treating a deprotected, resin-attached polyamide containing a primary amine group with commercially available N,N'-di-Boc-1H-pyrazole-1-carboxamide, followed by Boc removal. This synthetic route is illustrated in FIG. 4. See Robinson et al., *Tetetrahedron* 1997, 53 (19), 6697.

Figure 5:
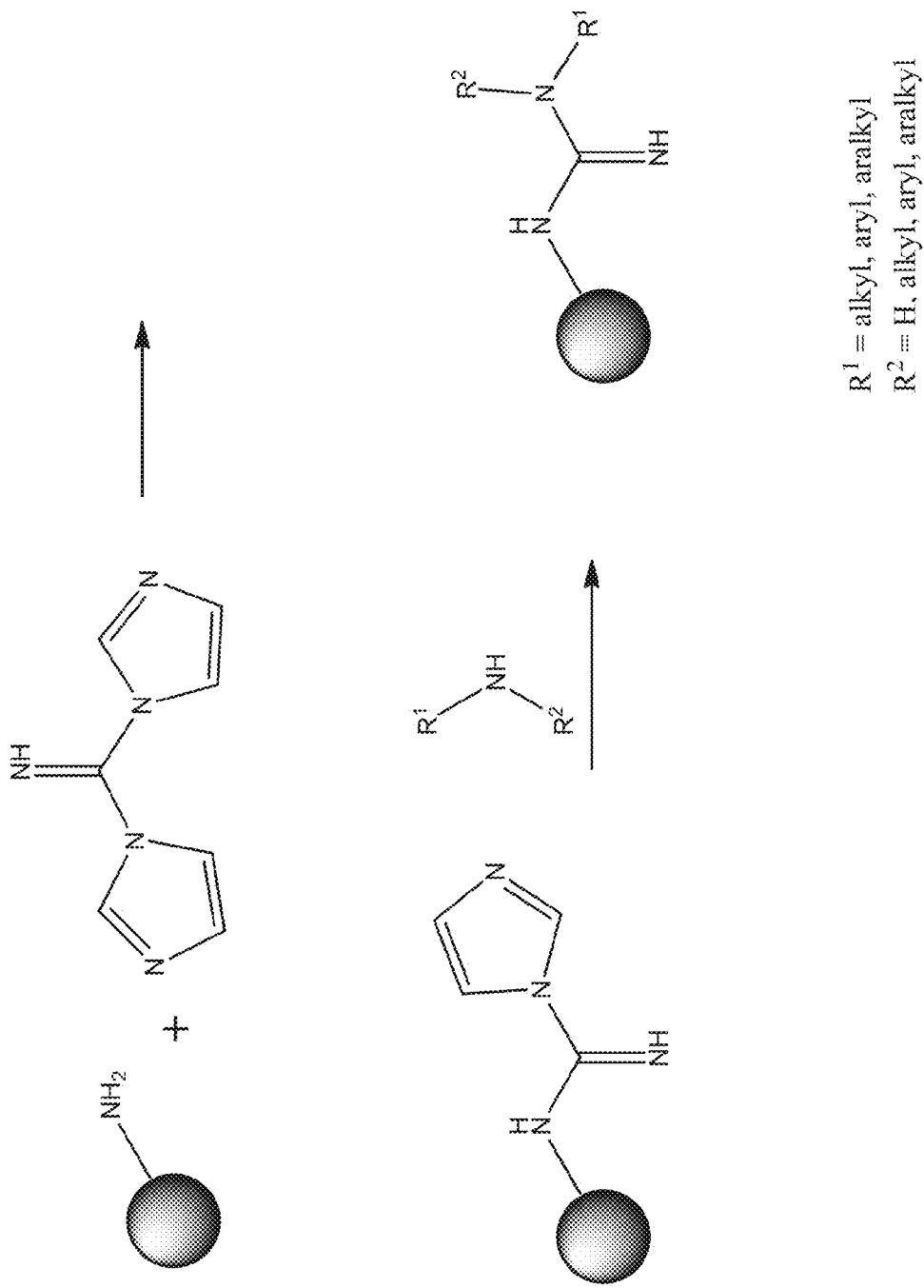
FIG. 5 illustrates a synthetic route that may be employed to provide a guanidinylated polyamide in accordance with the invention wherein the guanidinyl radical is monosubstituted or gem-disubstituted.

A monosubstituted or gem-disubstituted guanidinyl radical [$—NH—C(=NH)NHR$ or $—NH—C(=NH)NR_2$, where the R groups may be the same or different] may be introduced on the N-terminus of a polyamide by treating a deprotected, resin-attached polyamide containing a primary amine group with commercially available di(imidazole-1-yl)methanimine, followed by addition of a primary amine (to provide a monosubstituted guanidinyl radical) or a secondary amine (to provide a gem-disubstituted guanidinyl radical). This synthetic route is illustrated in FIG. 5. See Wu et al., *J. Org. Chem.* 2002, 67, 7553.

Figure 6:
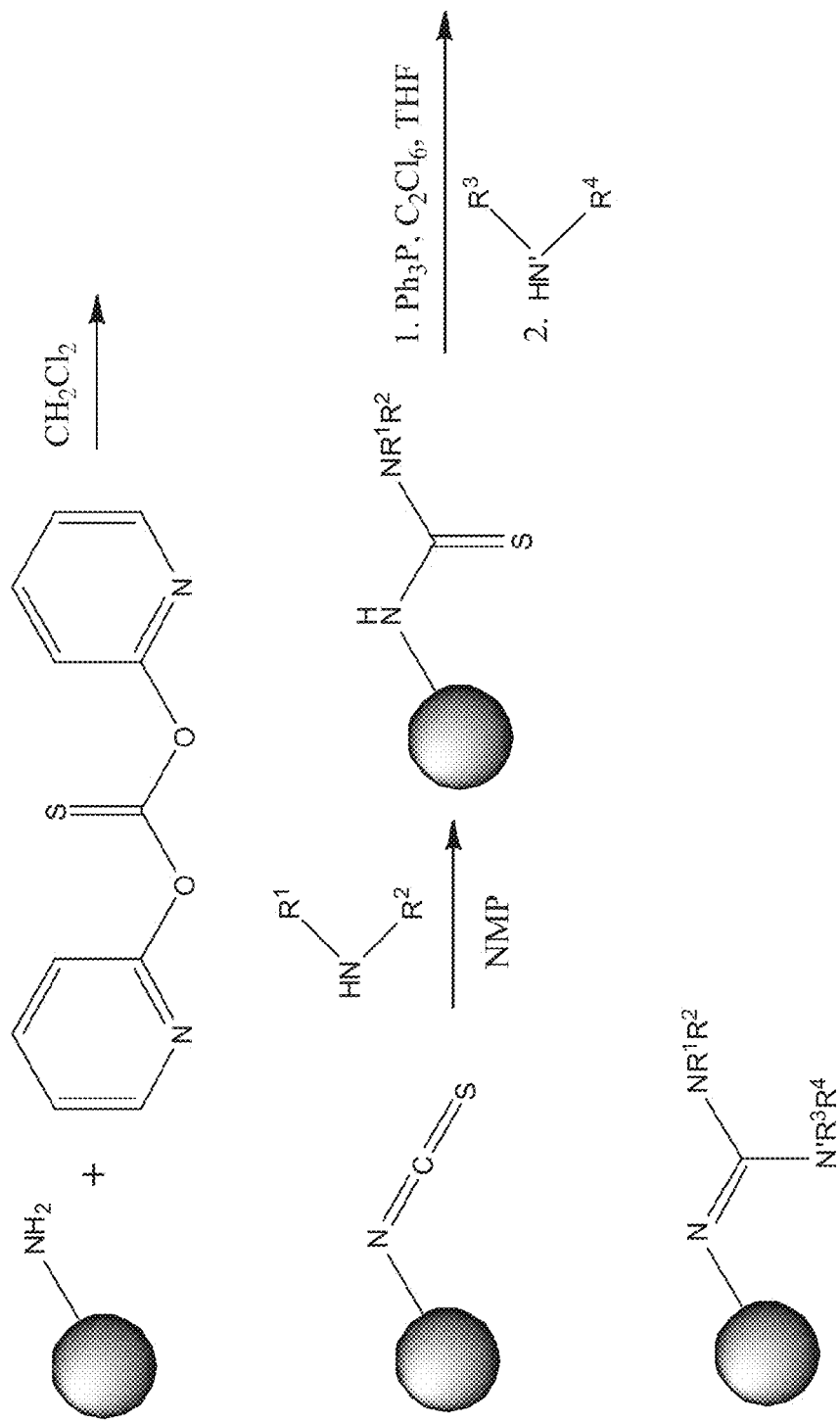
FIG. 6 illustrates a synthetic route which may be employed to provide a guanidinylated polyamide in accordance with the invention wherein the guanidinyl radical is N,N'-disubstituted, N,N,N'-trisubstituted, or N,N,N',N'-tetrasubstituted.

N,N'-disubstituted, N,N,N'-trisubstituted, or N,N,N',N'-tetrasubstituted guanidinyl groups [$—N=C(NHR)_2$, $—N=C(NHR)(NR_2)$, or $—N=C(NR_2)_2$, where in each case the R groups may be the same or different] may be introduced on the N-terminus of a polyamide by treating a deprotected, resin-attached polyamide containing a primary amine group with commercially available di-(2-pyridyl)thionocarbonate to give an intermediate isothiocyanate. Subsequent addition of a primary or secondary amine, desulfurization, and addition of another primary or secondary amine would provide the desired N,N'-disubstituted, N,N,N'-trisubstituted, or N,N,N',N'-tetrasubstituted guanidinylated polyamides as illustrated in FIG. 6. See Kilburn, J. P.; Lau, J.; Jones, R. C. F. *Tetrahedron* 2002, 58, 1739.

Figure 7:
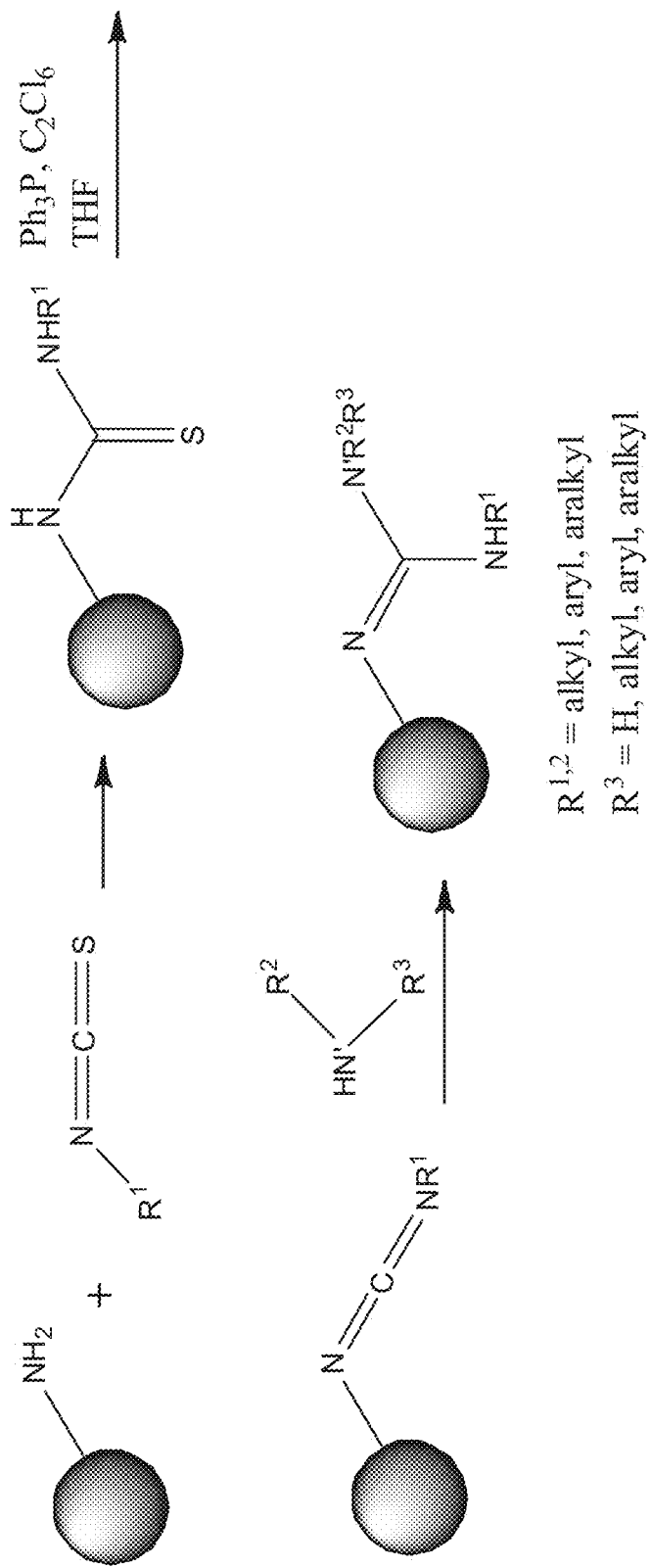
FIG. 7 illustrates a synthetic route which may be employed to provide a guanidinylated polyamide in accordance with the invention wherein the guanidinyl radical is N,N'-disubstituted or N,N',N'-trisubstituted.

Alternatively, N,N'-disubstituted or N,N,N'-trisubstituted guanidinyl groups [$—N=C(NHR)_2$ or $—N=C(NHR)(NR_2)$, where in each case the R groups may be the same or different] may be introduced on the N-terminus of a polyamide by treating a deprotected, resin-attached polyamide containing a primary amine group with an isothiocyanate (containing a first R group). Desulfurization would provide an intermediate carbodiimide Addition of a primary or secondary amine [containing the second R group(s)] to the carbodiimide would provide the desired N,N'-disubstituted or N,N',N'-trisubstituted guanidinylated polyamide, respectively, as illustrated in FIG. 7. See *Chemistry—A European Journal*, 11(5), 1459-1466, 2005, and Kilburn et al. *Tetrahedron* 2002, 58, 1739.

Pharmaceutical Compositions

Formulation

In another aspect of the present invention, pharmaceutically acceptable compositions are provided, wherein these compositions comprise any of the polyamide compounds as described herein, and optionally comprise a pharmaceutically acceptable carrier, adjuvant or vehicle. In certain embodiments, these compositions optionally further comprise one or more additional therapeutic agents.

Polyamides can be in the form of pharmaceutically acceptable salts such as trifluoroacetate (TFA) salts as well as chloride, succinate, ascorbate salts and the like. They can also be formulated with excipients such as PEG-400, propylene glycol and the like.

To increase stability, the polyamide drug may be placed in aqueous solution with an antioxidant such as ascorbic acid, BHT or BHA in order to develop a more stable formula. (See Mayers C. L., et al. (1993) *Pharma Res*, 10: 445-448, and Stuhar M., (1984) *Farmaceuticky Obzor*, 53; 499-504, both of which are incorporated herein by reference.)

For delivery to the vagina and cervix, polyamides may be formulated as solutions, emulsions, suspensions, tablets, gels, foams, suppositories, films, sponges and vaginal rings. Formulations include gels (e.g., gels prepared using gelling agents such as hydroxy ethyl cellulose and polyacrylic acids, e.g., cross-linked acrylic acid based polymers such as those sold under the brand name CARBOPOL), and polyvinyl alcohol films that can be administered by an applicator to the target site. Alternatively, lower viscosity liquid formulations (e.g. PEG solutions) can be delivered in a polyurethane sponge to the area around the cervix. (Okada, (1991) in "Peptide and Protein Drug Delivery" V. H. Lee, ed., pp. 663-666, Marcel Dekker, NY; Garg, et al. (2001) *Pharm. Tech.* 25:14-24, both of which are incorporated herein by reference.) Because of the polyamides' charge, the polyamides may be formulated in a controlled delivery vehicle by using carbomers (such as those sold under the brand name CARBOPOL). If the polyamide has a charge of +1 or +2, by adjusting the ionic strength of the formulation one may bind the polyamide electrostatically to the carbomer and thereby control the release rate. In a semisolid dosage form, the release rate may be evaluated in a membrane apparatus as described in the US Pharmacopeia (Dipiano, et al., PCT International Publication No. WO 04/064913, which is incorporated herein by reference) for drug diffusion from semisolid dosage forms. Polyamides formulated in carbomer-based gels which exhibit significant yield stresses, and also have potential bioadhesive properties (Kieweg, et al. (2004) *J. Pharm Sci.* 93, 2941-52, which is incorporated herein by reference).

Any of the excipients used for commercial vaginal formulations (Garg et al., 2001) may be adapted for use with the polyamide compounds of the present invention. A number of commonly used excipients such as PEG (polyethylene glycol), PVA (polyvinyl alcohol) and Tween surfactants can also be employed. In addition to antioxidants, further compatibilizers or stabilizers may be used. Solid forms may allow for more stable formulas with a longer shelf life due to their physical state. Emulsions made from bioadhesives using polymers such as carbomers may be useful. HPMC (hydroxymethylpropyl cellulose), PVA and lipid complexes can be used with lower solubility drugs. Lipidic systems may then be suspended in a viscoelastic gel for delivery of the insoluble polyamide.

For more sustained or effective delivery, cervical barrier devices available such as diaphragms that can deliver the drug at the cervix site over many hours can be used for delivery that is even more continuous vaginal rings or slow release implantable polymer films can be employed. In addition, several new vaginal delivery systems in clinical testing such as vaginal sponge technology and the SILCS diaphragm, a single size silicone device that can deliver drug to both the cervix and vaginal wall (Cohen, (2004) *The Microbiocide Quarterly*, 2:15-19, which is incorporated herein by reference) may be used. For improved continuous delivery of the drug over an extended period, vaginal rings are available with slow release of the drug from the ring composite (Cohen, 2004; Hussain and Ahsan, (2005), *J. Controlled Release* 103: 301-13, which is incorporated herein by reference). There are also numerous other applicators and formulas that have been developed for controlled vaginal drug delivery (Robinson (1999) *Proc. Of the 26th Intl. Symp. Controlled Release of Bioactive Materials*, 26:2-3, which is incorporated herein by reference; Hussain and Ahsan, 2005).

Formulations for transdermal delivery include lipid-based formulas for delivery of protein pharmaceuticals to genital warts (Foldvari et al., (1999), *Biotech. Appl. Biochem.* 30:129-37; Leigh (2003) *Drugs and the Pharm. Sci.*, 126: 791-800; Lee et al., (2004) *Biomaterials*, 26:205-10, all of which are incorporated herein by reference), bioadhesives formulations (Bogataj and Mrhar (1998) Bioadhesive mucosal drug delivery systems, 49:445-57; Amaral et al. (1999) *Contraception*, 60:361-66; Barry, (1987) in "Drug Delivery systems", Johnson and Lloyd-Jones, eds, Ch. 11, Ellis Horwood, Chichester; Vermani, et al. (2002) *Drug Dev. Indust. Pharm.* 28:1133-46, all of which are incorporated herein by reference) and novel polymer systems. The novel polymers include partially absorbable biodegradable antiviral intravaginal rings (Shalaby, (2005) U.S Patent Application Publication No. 2005/053639, which is incorporated herein by reference), bilaminar bioadhesive polymeric films applied directly to the cervix (Sidhu et al., (1997) *Br. J. Obstetrics and Gynaecology*, 104:145-49, which is incorporated herein by reference) novel, slow-release polymer discs at the cervical mucosa and thermogelling systems that have the advantage of potentially much greater bioadhesion and dosage form retention. (Saltzman and Radomsky (1990) *Polymer Preprints*, 31:245-46; Edelman and Mark (1998) *Nature Biotech*, 16:136-37, both of which are incorporated herein by reference). Polyamides may also be formulated using cell membrane penetrating peptides (Gupta, et al. (2005) *Adv. Drug Del Rev.* 57:637-51; Wadia and Dowdy (2005) *Adv. Drug Del. Rev.*, 57:579-96, both of which are incorporated herein by reference.

The polyamides of the present invention can also be formulated with a pharmaceutically-acceptable polymer designed to shorten or lengthen time before renal clearance.

Polyamides in accordance with the present invention can also be formulated to deliver an aerosol treatment of the lungs, mouth or throat. Direct injection into HPV lesions may also be employed for external (cutaneous) or mucosal skin infections.

Other disease indications may require systemic treatment with the present polyamides, i.e., by injection, or additional, common or known drug delivery methods.

It will also be appreciated that certain compounds of the present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a subject in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describes pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, including trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described above, the pharmaceutically acceptable compositions of the present invention comprise, in addition to one or more polyamide compounds, a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

According to the invention, an "effective amount" of the compound or pharmaceutically acceptable composition is that amount effective for treating or lessening the severity of HPV infections. If other indications are being treated with the polyamides described here, then an "effective amount" would be defined as per the norms of treatment for those diseases.

Administration

The pharmaceutical compositions, according to the method of the present invention, may be administered using any amount and any route of administration effective for treating or lessening the severity of a chronic HPV disease.

The exact amount required will vary from subject to subject, depending on the species, age, sex, weight, diet, medical condition and general condition of the subject, the severity of the infection, the particular agent, its mode of administration, and the like. Other factors affecting the dosing regimen include pharmacological considerations such as the activity, efficacy, pharmacokinetics and toxicology profiles of the compounds employed, whether a drug delivery system is used and whether the compounds are administered with other ingredients. The dosage can be determined routinely using standard methods known in the art. The dosage regimen actually employed may therefore vary widely based upon the treated subject and thus deviate from the exemplary dosage regimen set forth below. The compounds of the invention are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds and compositions of the present invention will be decided by the attending physician within the scope of sound medical judgment. The specific effective dose level for any particular subject will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed, and like factors known in the medical arts. The term "subject", as used herein, means an animal, for example, a mammal, including a human.

Administration of the compounds may be with a regimen calling for a single daily dose, multiple, spaced doses throughout the day, a single dose every other day, a single dose every several days or other appropriate regimens.

For example, the formulated polyamides can be administered once daily at a final concentration of 5 mg/mL (approximate concentration of 2.5 mM) in approximately 4 ml of vehicle via a vaginal applicator, for example, to the posterior fornix of the vagina. If administered in the evening prior to sleep, it is anticipated that most of the drug will remain in the highest aspects of the vaginal canal, in closest proximity to the cervix, due to lack of ambulation. In one embodiment, the polyamide formulation may be administered for 10 days.

The pharmaceutically acceptable compositions of this invention can be administered to humans and other animals orally, rectally, parenterally, intracistemally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid may be used in the preparation of injectables.

The injectable formulations can be sterilized, for example, by incorporating sterilizing agents in the form of sterile solid compositions that can be dissolved or dispersed in sterile water or other sterile injectable medium prior to use.

To prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration can be suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular-weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as treatments for HPV diseases, including chronic HPV diseases.

More than one compound of the invention may be administered separately, simultaneously, or sequentially to infected cells, to tissue containing the infected cells, or to infected subjects.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably, the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Methods of Treating

Another aspect of the invention relates to treating virus affected cells or other virus in a biological sample or a subject (e.g., in vitro or in vivo), which method comprises administering to the subject (human or other animal), or contacting said biological sample with a pharmaceutical composition comprising a polyamide as described herein. Mixtures of the polyamides described herein may also be employed. The term "biological sample", as used herein, includes, without limitation, cell cultures or extracts thereof; biopsied material obtained from a mammal or extracts thereof; and blood, saliva, urine, feces, semen, tears, or other body fluids or extracts thereof. The term "subject" includes animals, including mammals, humans, primates, dogs, cats, horses, pigs, cows, sheep and the like.

After the cells of an individual become exposed and infected with an HPV, a number of HPV episome copies may become established within an infected cell. The HPV episomes further replicate as the cells divide, forming approximately the same number of HPV episomal copies in each new cell (e.g., upon cell division, a cell containing 20-100 copies will form two new cells, each containing approximately 20-100 episome copies. Polyamides designed to target A/T-rich regions can promote the clearance of HPV episomes. Hence, the methods of the present invention can also be used beneficially as a therapeutic method to treat HPV.

The polyamides used to treat HPV or other papilloma viruses include, without limitation, those described herein.

In one embodiment, the invention provides a method of treating HPV affected cells comprising contacting the cells with a compound described herein or a mixture of such compounds. In an aspect of the invention, the method further comprises contacting the cells with an anti-viral agent. The anti-viral agent can be an Interferon, Imiquimod, cidofovir, formaldehyde, glutaral, cimetidine, 5-fluorouracil, tricholoroacetic acid, bleomycin, podofilox or podophyllum.

In another embodiment, the invention provides a method of treating HPV affected cells in a subject, comprising administering to a subject a compound or pharmaceutical composition described herein. In an aspect of the invention, the method further comprises contacting the cells with an anti-viral agent. The anti-viral agent can be an Interferon, Imiquimod, cidofovir, formaldehyde, glutaral, cimetidine, 5-fluorouracil, tricholoroacetic acid, bleomycin, podofilox or podophyllum. In another aspect, the HPV can be HPV 11, HPV16, HPV18, HPV1, HPV6 or HPV31.

In other embodiments, the invention provides a method of treating HPV16, HPV18 or HPV31 affected cells comprising administering to a subject a polyamide in accordance with the invention, in particular a compound of the formula $Z—(X)_n-\gamma^q-(X)_m-A$, or a pharmaceutically acceptable salt thereof, wherein Z, X, $\gamma^q$, A, m and n are as described above, or a compound of the formula $G-(X)_n-\gamma^q-(X)_m-A$, or a pharmaceutically acceptable salt thereof, wherein G, X, $\gamma^q$, A, m and n are as described above.

In yet other embodiments, the invention provides a method of treating HPV affected cells, such as HPV16, HPV18 or HPV31 affected cells, by administering to a subject a compound selected from:

TMG-PyPyβPyPyβPyIm-$\gamma_{NH2}$-PyβPyPyβPyPyPyβPyPy-Ta;

TMG-PyPyPyβPyPyβPyIm-$\gamma_{NHR'}$-PyβPyPyβPyPyPyβPyβ-Ta;

TMG-PyPyPyβPyPyβPyIm-$\gamma_{NH2}$-PyβPyPyβPyPyPyβPyβ-Ta;

TMG-PyPyPyβPyPyβPy-$\gamma_{NHR'}$-PyPyPyβPyPyPyβPyβ-Ta;

TMG-PyPyPyβPyPyβPyIm-$\gamma_{NH2}$-PyβPyPyβPyPyPyβPyβ-Dp;

TMG-PyPyPyβPyPyβPy-$\gamma_{NH2}$-PyPyPyβPyPyPyβPyβ-Ta;

TMG-PyPyPyβPyPyβPy-$\gamma_{NH2}$-PyPyPyβPyPyPyβPyβ-Dp;

TMG-PyβPyPyImβPyPy-γ-PyPyβPyPyPyβPyPyPyβ-Ta;

TMG-PyPyPyβPyPyβPy-$\gamma_{NHR''}$-PyPyPyβPyPyPyβPyβ-Dp;

TMG-PyβPyPyImβPyPy-γ-PyPyβPyPyPyPyβPyPyPyβ-Dp;
TMG-PyβPyPyPy-γ-PyPyβPyPyPyPyβ-Dp;
TMG-PyβPyPyPy-γ-PyPyβPyPyPyPyβ-Ta;
TMG-PyPyβPyPyPy-γ-PyPyβPyPyPyPyβ-Dp;
TMG-PyPyβPyPyPy-γ-PyPyβPyPyPyPyβ-Ta;
TMG-PyPyβPyPyImβPyPy-γ-PyPyβPyPyPyβPyPyPyβ-Ta;
TMG-PyPyβPyPyImβPyPy-γ-PyPyβPyPyPyβPyPyPyβ-Dp;
TMG-PyPyPyβPyPyβPyIm-γ-PyβPyPyβPyPyPyβPyβ-Ta;
TMG-PyPyPyβPyPyβPyIm-γ-PyβPyPyβPyPyPyβPyβ-Dp;
TMG-PyPyPyβPyPyβPyIm-γωPyβPyPyβPyPyPyβPyβ-Dp;
TMG-PyPyPyβPyPyβPyIm-γ-PyβPyPyβPyPyPyβPyβ-Ta;
TMG-PyImβPyPy-γ-PyPyPyβPyPyPyβ-Ta;
TMG-PyPyβPyPyPyβPy-γ$_{NH2}$-PyPyPyβPyPyPyβPyβ-Ta;
TMG-PyPyβPyPyβPyIm-γ$_{NH2}$-PyβPyPyβPyPyPyβPyβ-Ta;
TMG-PyPyβPyPyPyβPy-γ-PyPyPyβPyPyPyβPyβ-Ta;
TMG-PyPyPyβPyPyβPy-γ-PyPyPyβPyPyPyβPyβ-Ta;
TMG-PyImPyIm-γ-PyPyPyPyβ-Ta;
TMG-PyImβIm-γ-PyβPyPyβ-Ta;
TMG-PyImβPyIm-γ-PyβPyPyβ-Ta;
TMG-PyImβIm-γ-PyPyPyPyβ-Ta;
GUAN-PyImβImγPyβPyPyβ-Ta;
and pharmaceutically acceptable salts thereof.

In aspects of this embodiment, the method further comprises administering an antiviral agent. The antiviral agent can be an Interferon (e.g., Interferon-γ and Interferon-0), Imiquimod, cidofovir, formaldehyde, glutaral, cimetidine, 5-fluorouracil, trichloroacetic acid, bleomycin, podofilox, podophyllum, acyclovir and other Herpes/cytomegaloviral drugs, and anti-HIV drugs. The polyamides can also be used in combination with photodynamic therapy, radiation therapy and chemotherapy.

In order that the invention described herein may be more fully understood, the following examples are set forth. It should be understood that these examples are for illustrative purposes only and are not to be construed as limiting this invention in any manner.

Examples

Polyamide oligomers may be synthesized starting with Boc-β-alanine-PAM solid phase synthesis resin, or a similar commercially available resin such as Fmoc-β-alanine-Wang resin, adding building blocks as required for the target sequence. The final step in the preparation of a guanidinylated polyamide is exemplified by incorporation of a tetramethylguanidinyl (TMG) group at the N-terminus TMG-polyamide synthesis involves placement of the tetramethylguanidinyl radical using HATU (2-(7-aza-1H-benzotriazole-1-yl)-1,1,3,3-tetramethyluronium hexafluorophosphate).

Figure 2:
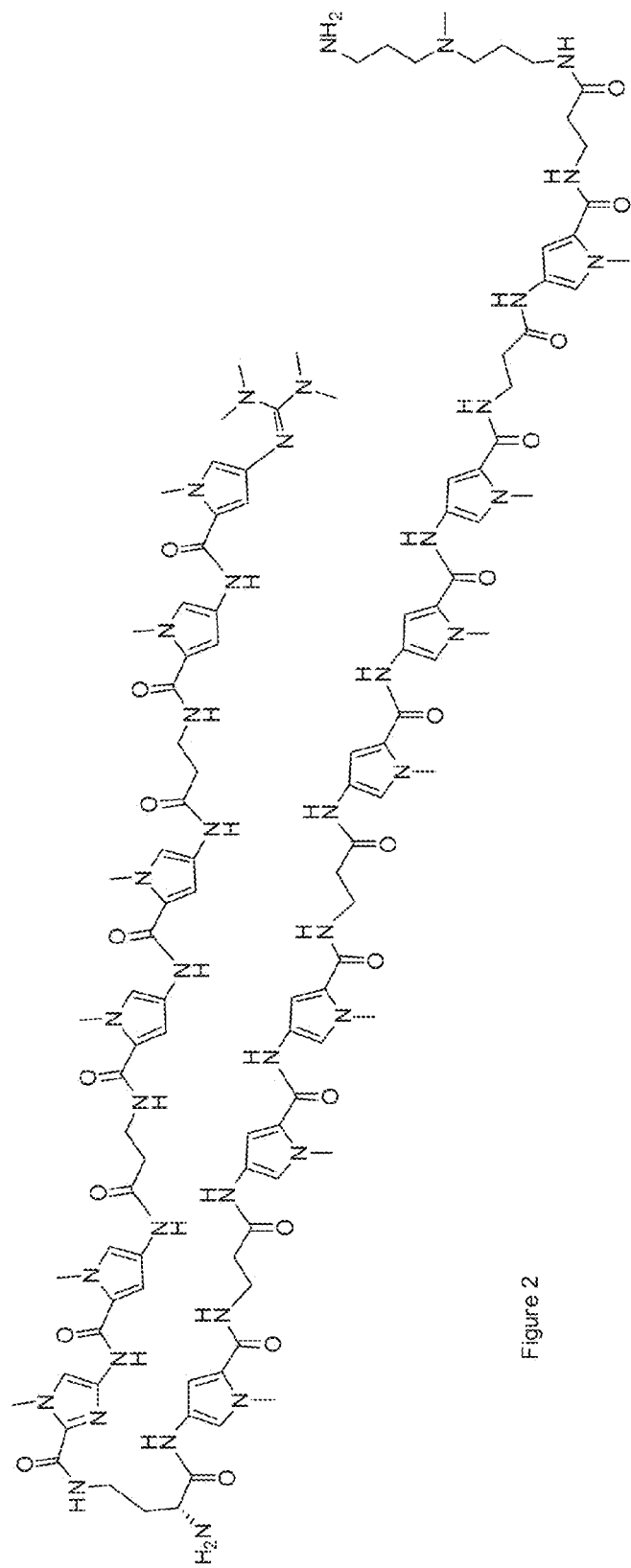
FIG. 2 illustrates the structure of a particular exemplary polyamide in accordance with the invention (compound NV1096).

Table 1a lists a number of exemplary polyamides synthesized in accordance with the present invention. The HPLC/MW values given in Table 1b were obtained using low resolution high pressure liquid chromatography/mass spectrometry (LR HPLC/MS), which provides moderate precision masses of single isotopomers rather than average molecular weights or exact masses. The full structure of compound NV1096 is set forth in FIG. 2. Table 2 presents a summary of measured IC$_{50}$ values of certain of these polyamides against HPV16, HPV18 and HPV31. The IC$_{50}$ is the concentration of compound required for 50% inhibition of viral replication in vitro. The polyamides were tested in cells that maintain HPV16, HPV18 or HPV31 DNA. Cells maintaining the selected HPV were cultured for 72 hours in the presence of the polyamide. Viral DNA was then quantified using real-time PCR and compared to vehicle (DMSO)-treated control cultures. The results obtained demonstrate that the tested polyamides generally exhibited effectiveness in inhibiting replication of HPV16, HPV18 and HPV31. Table 3 presents a summary of measured IC$_{50}$ and IC$_{90}$ values of certain of these polyamides against HPV16, HPV18 and HPV31. The results further demonstrate that the tested polyamides exhibited effectiveness in inhibiting replication of HPV16, HPV18 and HPV31.

TABLE 1a

| Compound | Structure |
| --- | --- |
| NV1071 | TMG-PyPyβPyPyβPyIm-γ$_{NH2}$-PyβPyPyβPyPyPyβPyPy-Ta•5TFA |
| NV1072 | TMG-PyPyPyβPyPyβPyIm-γ$_{NHR'}$-PyβPyPyβPyPyPyβPyβ-Ta•6TFA |
| NV1073 | TMG-PyPyPyβPyPyβPyIm-γ$_{NH2}$-PyβPyPyβPyPyPyβPyβ-Ta•5TFA |
| NV1074 | TMG-PyPyPyβPyPyβPy-γ$_{NHR'}$-PyPyPyβPyPyPyβPyβ-Ta•5TFA |
| NV1075 | TMG-PyPyPyβPyPyβPyIm-γ$_{NH2}$-PyβPyPyβPyPyPyβPyβ-Dp•4TFA |
| NV1076 | TMG-PyPyPyβPyPyβPy-γ$_{NH2}$-PyPyPyβPyPyPyβPyβ-Ta |
| NV1077 | TMG-PyPyPyβPyPyβPy-γ$_{NH2}$-PyPyPyβPyPyPyβPyβ-Dp |
| NV1078 | TMG-PyβPyPyImβPyPy-γ-PyPyβPyPyPyβPyPyPyβ-Ta•4TFA |
| NV1079 | TMG-PyPyPyβPyPyβPy-γ$_{NHR''}$-PyPyPyβPyPyPyβPyβ-Dp•3TFA |
| NV1080 | TMG-PyβPyPyImβPyPy-γ-PyPyβPyPyPyβPyPyPyβ-Dp•3TFA |
| NV1081 | TMG-PyβPyPyPy-γ-PyPyβPyPyPyPyβ-Dp•2TFA |
| NV1082 | TMG-PyβPyPyPy-γ-PyPyβPyPyPyPyβ-Ta•3TFA |
| NV1083 | TMG-PyPyβPyPyPy-γ-PyPyβPyPyPyPyβ-Dp•2TFA |
| NV1084 | TMG-PyPyβPyPyPy-γ-PyPyβPyPyPyPyβ-Ta•3TFA |
| NV1085 | TMG-PyPyβPyPyImβPyPy-γ-PyPyβPyPyPyβPyPyPyβ-Ta•4TFA |
| NV1086 | TMG-PyPyβPyPyImβPyPy-γ-PyPyβPyPyPyβPyPyPyβ-Dp•3TFA |
| NV1087 | TMG-PyPyPyβPyPyβPyIm-γ-PyβPyPyβPyPyPyβPyβ-Ta•4TFA |
| NV1088 | TMG-PyPyPyβPyPyβPyIm-γ-PyβPyPyβPyPyPyβPyβ-Dp•3TFA |
| NV1089 | TMG-PyPyPyβPyPyβPyIm-γ-PyβPyPyβPyPyPyβPyβ-Dp•3TFA |
| NV1090 | TMG-PyPyPyβPyPyβPyIm-γ-PyβPyPyβPyPyPyβPyβ-Ta•4TFA |
| NV1094 | TMG-PyImβPyPy-γ-PyPyPyβPyPyPyβ-Ta•4TFA |
| NV1095 | TMG-PyPyβPyPyPyβ-γ$_{NH2}$-PyPyPyβPyPyPyβPyβ-Ta•4TFA |
| NV1096 | TMG-PyPyβPyPyβPyIm-γ$_{NH2}$-PyβPyPyβPyPyPyβPβ-Ta•5TFA |
| NV1097 | TMG-PyPyβPyPyβPy-γ-PyPyPyβPyPyβPyβ-Ta•3TFA |
| NV1098 | TMG-PyPyPyβPyPyβPy-γ-PyPyPyβPyPyPyβPyβ-Ta•3TFA |
| NV1101 | TMG-PyPyPyβPyPyβPyIm-γ-PyβPyPyβPyPyPyβPyβ-Ta-FAM•3TFA |
| NV1102 | TMG-PyImPyIm-γ-PyPyPyPyβ-Ta•5TFA |
| NV1103 | TMG-PyImβIm-γ-PyβPyPyβ-Ta•5TFA |
| NV1104 | TMG-PyImPyIm-γ-PyβPyPyβ-Ta•5TFA |
| NV1105 | TMG-PyImβIm-γ-PyPyPyPyβ-Ta•5TFA |
| NV1106 | GUAN-PyImβIm-γ-PyβPyPyβ-Ta•5TFA |

GUAN = unsubstituted guanidine
R' = —CONHCH$_2$CH$_2$CH$_2$N(Me)CH$_2$CH$_2$CH$_2$NH$_2$
R'' = —CONHCH$_2$CH$_2$CH$_2$N(Me)$_2$
TMG = tetramethylguanidinyl
β = beta-alanine
Ta = 3,3'-diamino-N-methyldipropylamine
γ = gamma-aminobutyric acid
Dp = 3-(dimethylamino)propylamine
Py = 4-amino-2-carbonyl-N-methylpyrrole
Im = 4-amino-2-carbonyl-N-methylimidazole TABLE 1b

| Compound | Molecular formula of free base | calc. exact mass M | calc. avg. MW | HPLC/MW (ESI$^+$) | HRMS |
| --- | --- | --- | --- | --- | --- |
| NV1071 | C$_{114}$H$_{145}$N$_{41}$O$_{20}$ | 2408.159 | 2409.63 | 2409.8 [M + H]+ 1205.5 [M + 2H]$^{2+}$ | 2408.14725 [M]$^+$ |

TABLE 1b-continued

| Compound | Molecular formula of free base | calc. exact mass M | calc. avg. MW | HPLC/MW (ESI$^+$) | HRMS |
|---|---|---|---|---|---|
| NV1072 | $C_{125}H_{167}N_{45}O_{22}$ | 2650.3332 | 2651.95 | 1326.5 [M + 2H]$^{2+}$ | 2650.31905 [M]$^+$ |
| NV1073 | $C_{117}H_{150}N_{42}O_{21}$ | 2479.1961 | 2480.71 | 2481.0 [M + H]$^+$ 1241.0 [M + 2H]$^{2+}$ | 2479.18193 [M]$^+$ |
| NV1074 | $C_{117}H_{157}N_{41}O_{20}$ | 2456.2529 | 2457.76 | 2458.2 [M + H]$^+$ 1229.5 [M + 2H]$^{2+}$ | 2456.24158 [M]$^+$ |
| NV1075 | $C_{115}H_{145}N_{41}O_{21}$ | 2436.1539 | 2437.64 | 2438.2 [M + H]$^+$ 1219.5 [M + 2H]$^{2+}$ | 2436.14773 [M]$^+$ |
| NV1076 | $C_{109}H_{140}N_{38}O_{19}$ | 2285.1157 | 2286.52 | 2287.0 [M + H]$^+$ 1144.0 [M + 2H]$^{2+}$ | 2285.10297 [M]$^+$ |
| NV1077 | $C_{107}H_{135}N_{37}O_{19}$ | 2242.0735 | 2243.45 | 2244.0 [M + H]$^+$ 1122.3 [M + 2H]$^{2+}$ | 2242.0638 [M]$^+$ |
| NV1078 | $C_{114}H_{144}N_{40}O_{20}$ | 2393.1481 | 2394.62 | 2395.0 [M + H]$^+$ 1198.0 [M + 2H]$^{2+}$ | 2393.13581 [M]$^+$ |
| NV1079 | $C_{113}H_{147}N_{39}O_{20}$ | 2370.1685 | 2371.63 | 2372.0 [M + H]$^+$ 1186.5 [M + 2H]$^{2+}$ | 2370.15878 [M]$^+$ |
| NV1080 | $C_{112}H_{139}N_{39}O_{20}$ | 2350.1059 | 2351.55 | 2352.0 [M + H]$^+$ 1176.5 [M + 2H]$^{2+}$ | 2350.09462 [M]$^+$ |
| NV1081 | $C_{83}H_{106}N_{28}O_{14}$ | 1718.8443 | 1719.91 | 1720.5 [M + H]$^+$ 860.5 [M + 2H]$^{2+}$ | 1718.834 [M]$^+$ |
| NV1082 | $C_{85}H_{111}N_{29}O_{14}$ | 1761.8865 | 1762.98 | 1763.5 [M + H]$^+$ 882.0 [M + 2H]$^{2+}$ | 1761.8757 [M]$^+$ |
| NV1083 | $C_{89}H_{112}N_{30}O_{15}$ | 1840.8923 | 1842.03 | 1842.5 [M + H]$^+$ 921.5 [M + 2H]$^{2+}$ | 1840.88244 [M]$^+$ |
| NV1084 | $C_{91}H_{117}N_{31}O_{15}$ | 1883.9345 | 1885.1 | 1885.5 [M + H]$^+$ 943.0 [M + 2H]$^{2+}$ | 1883.92375 [M]$^+$ |
| NV1085 | $C_{120}H_{150}N_{42}O_{21}$ | 2515.1961 | 2516.74 | 2517.0 [M + H]$^+$ 1259.0 [M + 2H]$^{2+}$ | 2515.18393 [M]$^+$ |
| NV1086 | $C_{118}H_{145}N_{41}O_{21}$ | 2472.1539 | 2473.68 | 2474.0 [M + H]$^+$ 1237.5 [M + 2H]$^{2+}$ | 2472.14515 [M]$^+$ |
| NV1087 | $C_{117}H_{149}N_{41}O_{21}$ | 2464.1852 | 2465.7 | 2466.0 [M + H]$^+$ 1233.5 [M + 2H]$^{2+}$ | 2464.1686 [M]$^+$ |
| NV1088 | $C_{115}H_{144}N_{40}O_{21}$ | 2421.143 | 2422.63 | 2423.0 [M + H]$^+$ 1212.0 [M + 2H]$^{2+}$ | 2421.12661 [M]$^+$ |
| NV1089 | $C_{109}H_{138}N_{38}O_{20}$ | 2299.095 | 2300.5 | 2300.8 [M + H]$^+$ 1151.0 [M + 2H]$^{2+}$ | 2299.116 [M]$^+$ |
| NV1090 | $C_{111}H_{143}N_{39}O_{20}$ | 2342.1372 | 2343.57 | 2343.8 [M + H]$^+$ 1172.5 [M + 2H]$^{2+}$ | 2342.15 [M]$^+$ |
| NV1094 | $C_{84}H_{110}N_{30}O_{14}$ | 1762.8818 | 1763.96 | 1763.8 [M + H]$^+$ 882.5 [M + 2H]$^{2+}$ | 1762.8907 [M]$^+$ |
| NV1095 | $C_{103}H_{134}N_{36}O_{18}$ | 2163.0677 | 2164.4 | 1083.0 [M + 2H]$^{2+}$ | |
| NV1096 | $C_{111}H_{144}N_{40}O_{20}$ | 2357.1481 | 2358.59 | 1180.0 [M + 2H]$^{2+}$ | 2358.17183 [M + H]$^+$ |
| NV1097 | $C_{103}H_{133}N_{35}O_{18}$ | 2148.0574 | 2149.39 | 2149.8 [M + H]$^+$ 1075.5 [M + 2H]$^{2+}$ | 2148.051 [M]$^+$ |
| NV1098 | $C_{109}H_{139}N_{37}O_{19}$ | 2270.1054 | 2271.51 | 2271.8 [M + H]$^+$ 1136.5 [M + 2H]$^{2+}$ | |
| NV1101 | $C_{138}H_{160}N_{41}O_{27}$ | 2823.2407 | 2825.01 | 1412.5 [M + 2H]$^{2+}$ | |
| NV1102 | $C_{65}H_{87}N_{25}O_{10}$ | 1377.70716 | 1378.56 | 1378.6 [M + H]$^+$ 689.8 [M + 2H]$^{2+}$ | 1377.7012 |
| NV1103 | $C_{59}H_{85}N_{23}O_{10}$ | 1275.6801 | 1276.46 | 1276.6 [M + H]$^+$ 638.8 [M + 2H]$^{2+}$ | 1275.6801 |
| NV1104 | $C_{62}H_{86}N_{24}O_{10}$ | 1326.69626 | 1327.51 | 1327.6 [M + H]$^+$ 664.4 [M + 2H]$^{2+}$ | 1326.6897 |

TABLE 1b-continued

| Compound | Molecular formula of free base | calc. exact mass M | calc. avg. MW | HPLC/MW (ESI+) | HRMS |
|---|---|---|---|---|---|
| NV1105 | $C_{62}H_{86}N_{24}O_{10}$ | 1326.69626 | 1327.51 | 1327.6 $[M + H]^+$ 664.4 $[M + 2H]^{2+}$ | 1326.69 |
| NV1106 | $C_{55}H_{77}N_{23}O_{10}$ | 1219.6227 | 1220.35 | 1220.4 $[M + H]^+$ 610.8 $[M + 2H]^{2+}$ | 2408.14725 $[M]^+$ |

TABLE 2

| Compound | HPV16 $IC_{50}$ | HPV18 $IC_{50}$ | HPV31 $IC_{50}$ |
|---|---|---|---|
| NV1071 | 0.255 | 0.093 | 0.095 |
| NV1072 | 0.109 | 0.216 | 0.096 |
| NV1073 | 0.267 | 0.405 | 0.220 |
| NV1074 | 0.178 | 0.041 | 0.052 |
| NV1075 | 0.124 | 0.049 | 0.056 |
| NV1076 | 0.067 | 0.048 | 0.104 |
| NV1077 | 0.095 | 0.015 | 0.032 |
| NV1078 | 0.032 | 0.027 | 0.035 |
| NV1079 | 0.042 | 0.017 | 0.037 |
| NV1080 | 0.053 | 0.035 | 0.047 |
| NV1081 | — | — | — |
| NV1082 | — | — | — |
| NV1083 | 2.41 | 0.929 | 3.082 |
| NV1084 | 1.91 | 1.041 | 7.325 |
| NV1085 | 0.029 | 0.041 | 0.032 |
| NV1086 | 0.043 | 0.062 | 0.016 |
| NV1087 | 0.031 | 0.024 | 0.016 |
| NV1088 | 0.02 | 0.035 | 0.014 |
| NV1089 | 0.068 | 0.068 | 0.046 |
| NV1090 | 0.051 | 0.053 | 0.022 |
| NV1094 | — | — | — |
| NV1095 | 0.204 | — | 0.049 |
| NV1096 | 0.024 | 0.036 | 0.035 |
| NV1097 | 0.07 | 0.257 | 0.04 |
| NV1098 | 0.011 | 0.017 | 0.024 |

In Table 2, "-" indicates no measurable antiviral response was obtained relative to control at the highest dose tested (10 µM).

TABLE 3

| Compound | HPV16 $IC_{50}$ | HPV16 $IC_{90}$ | HPV18 $IC_{50}$ | HPV18 $IC_{90}$ | HPV31 $IC_{50}$ | HPV31 $IC_{90}$ |
|---|---|---|---|---|---|---|
| NV1097 | 0.070 (±0.0002) | 1.407 | 0.257 (±0.041) | >10 | 0.040 (±0.001) | 10 |
| NV1098 | 0.011 (±0.0001) | 1.360 | 0.017 (±0.0001) | >10 | 0.024 (±0.001) | 0.549 |

Several alternative approaches may be used to confirm the effects of the compounds on viral DNA. These additional procedures include normalization to total DNA, preparation of DNA by different procedures including DNeasy (Total Genomic DNA) Qiagen spin columns, DNAzol total genomic DNA preparations, and Hirt (low MW DNA preparations; (Hirt, (1967), J Mol Biol. 26:365-9).

Southern blotting may be used to confirm the effects of polyamides on HPV DNA levels that were determined using real-time PCR technology. The experiments may be conducted as previously described (Gamer-Hamrick and Fisher, Virology, 301, 334-41, 2002).

The toxicity of each polyamide found active against HPV may be monitored in normal human keratinocytes using an MTT cell viability assay (Denizot and Lang, 1986).

OTHER EMBODIMENTS

It is to be understood that while the invention has been described in conjunction with the foregoing detailed description, the foregoing description is intended to illustrate and not limit the scope of the invention, which is defined by the scope of the appended claims. Other advantages, and modifications are within the scope of the following claims.

What is claimed is:

1. A compound of the formula:

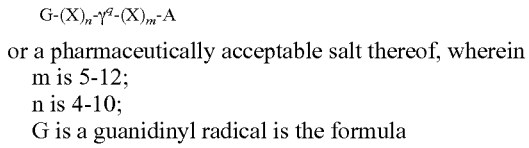

$G-(X)_n-\gamma^q-(X)_m-A$ or a pharmaceutically acceptable salt thereof, wherein
m is 5-12;
n is 4-10;
G is a guanidinyl radical is the formula

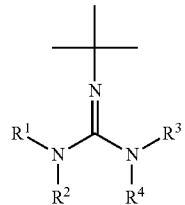

or its tautomer, wherein $R^1$, $R^2$, $R^3$, or $R^4$ is H, alkyl, aryl or aralkyl;
each X is independently selected from 4-amino-2-carbonyl-N-methylimidazole (Im), 4-amino-2-carbonyl-N-methylpyrrole (Py) or β-alanine (β);
$\gamma^q$ is γ-aminobutyric acid (γ), 2,4-diaminobutyric acid ($\gamma_{NH2}$), or $H_2N(CH_2)_2CH(NHC(=O)NHR)CO_2H$, wherein R is $-(CH_2)_3-N(CH_3)-(CH_2)_3-NH_2$ ($\gamma_{NHR'}$) or $-(CH_2)_3-N(CH_3)_2$ ($\gamma_{NHR''}$); and
A is 3,3'-diamino-N-methyldipropylamine (Ta) or 3-(dimethylamino)propylamine (Dp).

2. A compound according to claim 1, wherein G is tetramethylguanidinyl (TMG).

3. A compound according to claim 1, wherein the polyamide compound is selected from the group consisting of:
TM-PyPyβPyPyβPyIm-$\gamma_{NH2}$-PyβPyPyβPyPyPyβPyPy-Ta;
TMG-PyPyPyβPyPyβPyIm-$\gamma_{NHR}$-PyβPyPyβPyPyPyβ-Pyβ-Ta;
TMG-PyPyPyβPyPyβPyIm-$\gamma_{NH2}$-PyβPyPyβPyPyPyβ-Pyβ-Ta;
TMG-PyPyβPyPyβPy-$\gamma_{NHR}$-PyPyPyβPyPyPyβPyβ-Ta;
TMG-PyPyPyβPyPyβPyIm-$\gamma_{NH2}$-PyβPyPyβPyPyPyβ-Pyβ-Dp;

TMG-PyPyPyβPyPyβPy-γ_{NH2}-PyPyPyβPyPyPyβPyβ-Ta;
TMG-PyPyPyβPyPyβPy-γ_{NH2}PyPyPyβPyPyPyβPyβ-Dp;
TMG-PyβPyPyImβPyPy-γ-PyPyβPyPyPyβPyPyPyβ-Ta;
TMG-PyPyPyβPyPyβPy-γ_{NHR}-PyPyPyβPyPyPyβPyβ-Dp;
TMG-PyβPyPyImβPyPy-γ-PyPyβPyPyPyβPyPyPyβ-Dp;
TMG-PyβPyPyPy-γ-PyPyβPyPyPyPyβ-Dp;
TMG-PyβPyPyPy-γ-PyPyβPyPyPyPyβ-Ta;
TMG-PyPyβPyPyPy-γ-PyPyβPyPyPyPyβ-Dp;
TMG-PyPyβPyPyPy-γ-PyPyβPyPyPyPyβ-Ta;
TMG-PyPyβPyPyImβPyPy-γ-PyPyβPyPyPyβPyPyPyβ-Ta;
TMG-PyPyβPyPyImβPyPy-γ-PyPyβPyPyPyβPyPyPyβ-Dp;
TMG-PyPyPyβPyPyβPyIm-γ-PyβPyPyβPyPyPyβPyβ-Ta;
TMG-PyPyPyβPyPyβPyIm-γ-PyβPyPyβPyPyPyβPyβ-Dp;
TMG-PyPyβPyPyβPyIm-γ-PyβPyPyβPyPyPyβPyβ-Dp;
TMG-PyPyβPyPyβPyIm-γ-PyβPyPyβPyPyPyβPyβ-Ta;
TMG-PyImβPyPy-γ-PyPyPyβPyPyPyβ-Ta;
TMG-PyPyβPyPyβPy-γ_{NH2}-PyPyPyβPyPyPyβPyβ-Ta;
TMG-PyPyβPyPyβPyIm-γ_{NH2}-Py βPyPyβPyPyPyβPyβ-Ta;
TMG-PyPyβPyPyβPy-γ-PyPyPyβPyPyPyβPyβ-Ta;
TMG-PyPyPyβPyPyβPy-γ-PyPyPyβPyPyPyβPyβ-Ta;
TMG-PyImPyIm-γ-PyPyPyPyβ-Ta;
TMG-PyImβIm-γ-PyβPyPyβ-Ta;
TMG-PyImPyIm-γ-PyβPyPyβ-Ta;
TMG-PyImβIm-γ-PyPyPyPyβ-Ta;
GUAN-PyImβImγPyβPyPyβ-Ta;
and pharmaceutically acceptable salts thereof.

4. A compound according to claim 1, wherein $\gamma^q$ is (R)-2,4-diaminobutyric acid ($\gamma_{NH2}$).

5. A compound according to claim 1, wherein $\gamma^q$ is (S)-2,4-diaminobutyric acid ($\gamma_{NH2}$).

6. A pharmaceutical composition comprising a therapeutically effective amount of a compound of claim 1 and a pharmaceutically acceptable carrier.

7. The compound according to claim 1, which is fluorescent or fluorescently labeled.

8. The compound according to claim 7, of formula:
TMG-PyPyPyβPyPyβPyIm-γ-PyβPyPyβPyPyPyβPyβ-Ta-FAM; and pharmaceutically acceptable salts thereof.

9. A method of treating virus infected cells comprising contacting the cells with an effective amount of a compound of claim 1.

10. The method according to claim 9, wherein the infection is caused by a double-stranded DNA virus.

11. The method according to claim 9, wherein the infection is caused by HPV, Epstein-Barr viruses, herpes viruses, adenoviruses, BK and pox viruses.

12. The method according to claim 9, wherein the infection is caused by HPV16, HPV31, or HPV18.

13. A method of treating HPV in a subject comprising administering to the subject a pharmaceutical composition comprising an effective amount of a compound of claim 1 and a pharmaceutically acceptable carrier.

* * * * *

UNITED STATES PATENT AND TRADEMARK OFFICE
CERTIFICATE OF CORRECTION

| | |
|---|---|
| PATENT NO. | : 9,133,228 B2 |
| APPLICATION NO. | : 13/649000 |
| DATED | : September 15, 2015 |
| INVENTOR(S) | : James K. Bashkin et al. |

It is certified that error appears in the above-identified patent and that said Letters Patent is hereby corrected as shown below:

On the Title Page, Item (56)

Page 2, Other Publications, Edelson, et al.,: "structure" should be --structural--.

Page 2, Other Publications, Livengood, et al.,: "pp. 3056-3067" should be --pp. 3058-3067--.

In the Claims

Column 34, Line 24: "is the formula" should be --comprising the formula--.

Column 34, Line 54: "TM-Py" should be --TMG-Py--.

Signed and Sealed this
Tenth Day of November, 2015

Michelle K. Lee
*Director of the United States Patent and Trademark Office*